United States Patent
Liu et al.

(10) Patent No.: US 9,956,187 B2
(45) Date of Patent: May 1, 2018

(54) COMPOSITIONS AND METHODS FOR TREATING OPIOID RECEPTOR ASSOCIATED DISEASES

(71) Applicant: THE TRUSTEES OF THE UNIVERSITY OF PENNSYLVANIA, Philadelphia, PA (US)

(72) Inventors: Renyu Liu, Media, PA (US); Geoffrey Krug, Glen Mills, PA (US); Feixiang Wu, Shanghai (CN); Julie Blendy, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days. days.

(21) Appl. No.: 15/303,221

(22) PCT Filed: Apr. 9, 2015

(86) PCT No.: PCT/US2015/025090
§ 371 (c)(1),
(2) Date: Oct. 10, 2016

(87) PCT Pub. No.: WO2015/157509
PCT Pub. Date: Oct. 15, 2015

(65) Prior Publication Data
US 2017/0027887 A1 Feb. 2, 2017

Related U.S. Application Data

(60) Provisional application No. 61/978,005, filed on Apr. 10, 2014.

(51) Int. Cl.
*A61K 31/135* (2006.01)
*A61K 9/51* (2006.01)
*A61K 9/00* (2006.01)
*A61K 31/4178* (2006.01)
*A61K 45/06* (2006.01)
*A61K 31/485* (2006.01)

(52) U.S. Cl.
CPC .......... *A61K 31/135* (2013.01); *A61K 9/0019* (2013.01); *A61K 9/0043* (2013.01); *A61K 9/5123* (2013.01); *A61K 9/5138* (2013.01); *A61K 9/5161* (2013.01); *A61K 31/4178* (2013.01); *A61K 31/485* (2013.01); *A61K 45/06* (2013.01)

(58) Field of Classification Search
CPC .. A61K 31/135; A61K 9/5123; A61K 9/5138; A61K 9/5161; A61K 9/0043; A61K 9/0019; A61K 31/4178; A61K 45/06; A61K 31/485
See application file for complete search history.

(56) References Cited

U.S. PATENT DOCUMENTS

2004/0209850 A1* 10/2004 Babul ................ A61K 31/365
514/165
2012/0065221 A1* 3/2012 Babul ................ A61K 9/0004
514/289

* cited by examiner

*Primary Examiner* — Trevor Love
(74) *Attorney, Agent, or Firm* — Mark S. Cohen; Pearl Cohen Zedek Latzer Baratz LLP

(57) ABSTRACT

The invention relates to dezocine compositions and uses thereof. Specifically, the invention relates to dezocine compositions, including nano-dezocine compositions and methods for preventing or treating opioid receptor associated diseases, including neuropathic pain; addiction, such as opioid or cocaine addiction; and depression.

7 Claims, 18 Drawing Sheets

Figure 3
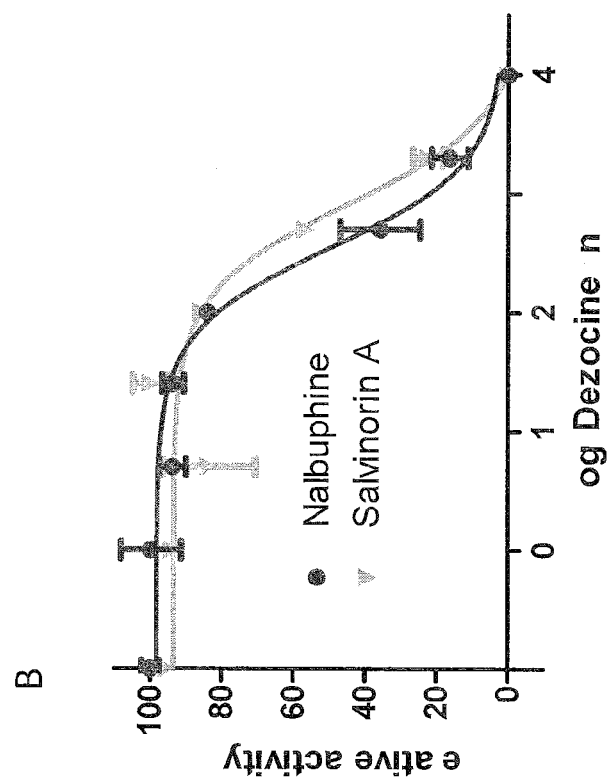
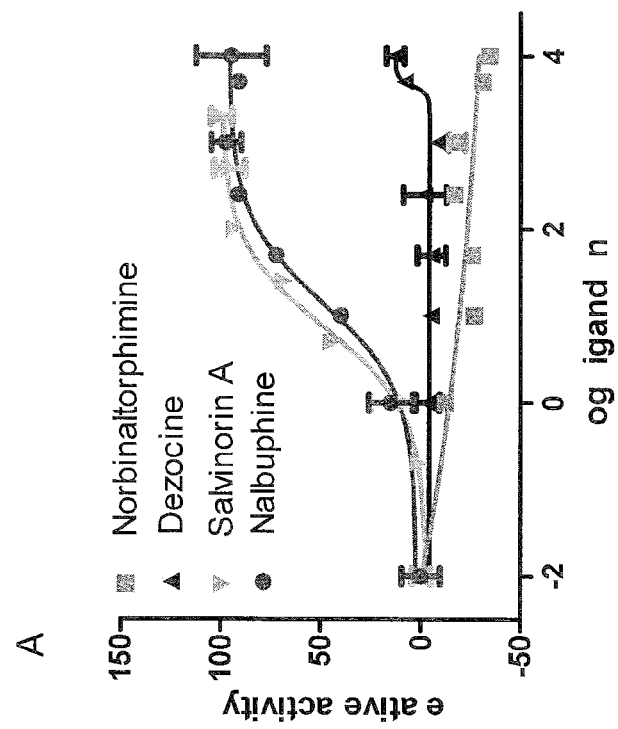

Figure 6    A (hSERT model)    B (LeuT crystal structure, 2QJU)

Figure 13
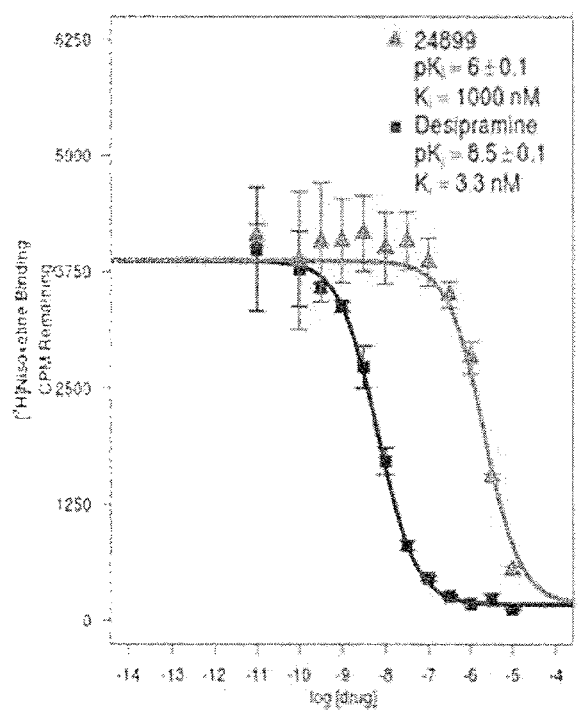
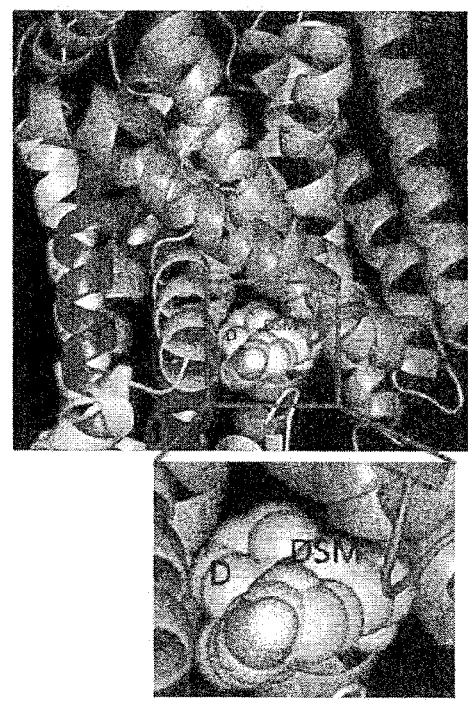

A rat without dezocine treatment

Two dezocine treated rats appear normal

HPLC C-18 column

COMPOSITIONS AND METHODS FOR TREATING OPIOID RECEPTOR ASSOCIATED DISEASES

CROSS-REFERENCE TO RELATED APPLICATIONS

This application is a National Phase Application of PCT International Application No. PCT/US2015/025090, filed on Apr. 9, 2015, claiming priority of U.S. Provisional Patent Application No. 61/978,008, filed Apr. 10, 2014, which are hereby incorporated by reference.

FIELD OF THE INVENTION

The invention relates to dezocine ($C_{16}H_{23}NO$) compositions and uses thereof. Specifically, the invention relates to dezocine compositions, including nano-dezocine compositions and methods for preventing or treating opioid receptor associated diseases, including neuropathic pain; addiction, such as opioid or cocaine addiction; and depression.

BACKGROUND OF THE INVENTION

The therapeutic use and abuse of opioids has soared in the United States and other countries in recent years. It is estimated that 79.5 million prescriptions for opioid analgesics were filled in 2009 in the US alone. Sales of methadone and oxycodone have increased 1,180% and 730% from 1997 to 2006, respectively. According to a Center for Disease Control (CDC) study, opioid analgesics have contributed to an increasing number of deaths in the United States. The number of fatal opioid analgesic poisonings has increased by 91% between 1999 and 2002. Methadone-related deaths have increased by 390% from 1999 to 2004. Drug overdoses and brain damage associated with long-term drug abuse killed an estimated 37,485 people in 2009. This surpassed the number of deaths attributed to traffic accidents of that year by 1,201. In addition to the human toll, opioid abuse has been estimated to contribute up to $300 billion per year in direct healthcare costs.

Many full opioid receptor agonists such as morphine, methadone, oxycodone and fentanyl are currently in the market for moderate and severe pain management. While these opioid medications provide pain relief to millions of patients, they also cause various devastating side effects. The side effects, which include respiratory depression, addiction, death, constipation and pruritus, are difficult to prevent or treat.

Recently, the use of partial agonists and antagonists as pain medications is increasing in popularity because of their improved side-effect profiles, especially decreased respiratory depression. Within this pharmacological class, buprenorphine is becoming the dominant medication for pain management as a partial agonist and partial antagonist of the mu opioid receptor. However, there are problems associated with the use of buprenorphine. First, buprenorphine is a Drug Enforcement Administration (DEA) schedule III medication whose use and distribution are regulated. Moreover, buprenorphine can cause addition by itself and such addiction is very difficult to manage. Furthermore, its tight binding with the opioid receptor makes it difficult to titrate and it takes 3-5 days for the medication to be eliminated from the body when full agonist opioids are needed for acute pain management and other opioid receptor associated diseases or disorders.

Accordingly, there exists a need for better medications and treatments for preventing or treating opioid receptor associated diseases or disorders.

SUMMARY OF THE INVENTION

In one aspect, methods are provided for preventing or treating an opioid receptor associated disease or disorder in a subject, the methods comprising: administering to said subject a therapeutically effective amount of dezocine or a pharmaceutical composition thereof (e.g., compositions of the dezocine nanoparticles or microparticles described herein).

In another aspect, methods are provided for preventing or treating neuropathic pain (NP) in a subject, the methods comprising: administering to said subject a therapeutically effective amount of dezocine or a pharmaceutical composition thereof (e.g., compositions of the dezocine nanoparticles or microparticles described herein).

In another aspect, methods are provided for preventing or preventing or treating an addiction disease (e.g., addition to heroin or cocaine) in a subject, the methods comprising: administering to said subject a therapeutically effective amount of dezocine or a pharmaceutical composition thereof (e.g., compositions of the dezocine nanoparticles or microparticles described herein).

In another aspect, methods are provided for preventing or treating depression in a subject, the methods comprising: administering to said subject a therapeutically effective amount of dezocine or a pharmaceutical composition thereof (e.g., compositions of the dezocine nanoparticles or microparticles described herein).

In another aspect, compositions are provided, the compositions comprising: dezocine and a second active agent selected from serotonin receptor inhibitors (e.g., ondansetron); or a opioid receptor antagonist, including but not limited to naloxone or naltrexone; or a mu opioid receptor agonist, including but not limited to morphine, methadone, or fentanyl; or a partial mu agonist; or a serotonin transporter inhibitor. In some embodiments the dezocine is present in an amount effective to treat an opioid receptor associated disease or disorder in a subject and the second agent is present in an effective amount to reduce a dezocine related adverse effect or in an effect effective amount to enhance the effect of the dezocine. In another example, the dezocine is present in an effective amount to reduce an adverse effect of the second active agent (e.g., the second active agent is an opioid agonist and the adverse effect is addiction) or in an effective amount to enhance the effect of the second active agent.

In another aspect, compositions are provided, the compositions comprising opioid nanoparticles, wherein the nanoparticle size is on the order of nanometers (nm). In another aspect, compositions are provided, the compositions comprising opioid nanoparticles, wherein the nanoparticle size is on the order of micrometers (μm). In some embodiments, the opioid nanoparticles are dezocine nanoparticles. In some embodiments, the forgoing compositions are adapted for extended or controlled release. In some embodiments, the foregoing compositions further comprise one or more additional active agents.

In another aspect, processes are provided for preparing opioid (e.g., dezocine) nanoparticles, the processes comprising the steps of: (a) preparing opioid (e.g., dezocine) in solution, (b) preparing a solution comprising poly(vinyl alcohol) (PVOH) and Propylene Glycol; (c) adding opioid (e.g., dezocine) to said solution comprising PVOH and Propylene Glycol; (d) homogenizing the resulting mixture until forming a nano-emulsion; (e) freezing and thawing said nano-emulsion for a predetermined time to produce hydrogel opioid nanoparticles or opioid nanoparticles; (f) filtering the opioid nanoparticles; and (g) suspending the opioid nanoparticles in solution.

In another aspect, provided herein are pharmaceutical compositions of opioids (e.g., dezocine), the compositions comprising: an aqueous solution of the opioid and a cyclodextrin.

In another aspect, methods are provided for preventing or preventing or treating opioid addiction in a subject, the methods comprising: administering to said subject a therapeutically effective amount of dezocine nanoparticles.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 3. A) Nalbuphine and salvinorin A, full agonists of kappa opioid receptors, concentration dependently activate the G protein in the presence of kappa receptor. Dezocine fails to induce any G protein activation, indicating receptor antagonism. Based on the activity of the G protein in its presence, nor-binaltorphimine is an inverse agonist of kappa opioid receptor. B) G protein was pre-activated with a full agonist (Nalbuphine, 250 nM or Salvinorin A, 20 nM) and then increasing amounts of dezocine was added. Dezocine inhibited the agonist effects of nalbuphine and salvinorin A concentration-dependently with a total blockage at high concentration, confirming the kappa receptor antagonism effect of dezocine. The relationship is plotted using the following model: Y=Bottom+(Top-Bottom)/(1+10^((Log EC$_{50}$-X)*HillSlope)).

FIG. 13. Left panel: The affinity of dezocine (24899, 1 μM) with NET. Right panel: The binding site of dezocine (D) in NET overlaps with desipramine (DSM), an antidepressant.

DETAILED DESCRIPTION OF THE INVENTION

Figure 1:
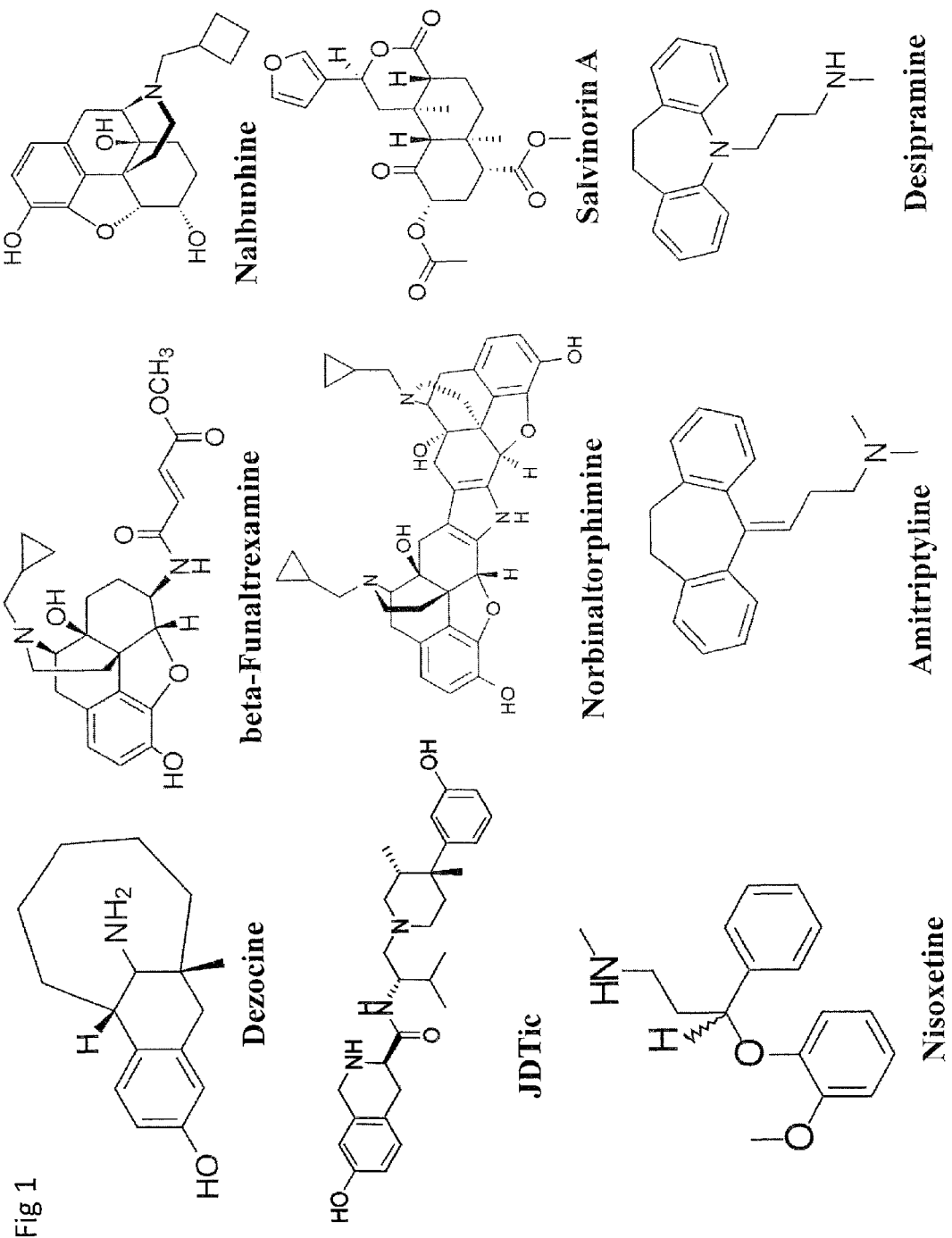
FIG. 1. The structures of ligands used herein to probe the pharmacological properties of dezocine are listed. All structures were obtained from public domain without further modification or verification, except for salvinorin A and JDTic. Salvinorin A and JDTic are obtained from Wikimedia Commons and are licensed under the Creative Commons Attribution-Share Alike 3.0 Unported license for free distribution with proper citation.

The invention relates to dezocine compositions and uses thereof. Specifically, the invention relates to dezocine compositions, including nano-dezocine compositions and methods for preventing or treating opioid receptor associated diseases, including neuropathic pain, addiction, and depression. The present inventors surprisingly and unexpectedly found that dezocine compositions can be used to treat opioid receptor associated diseases, including neuropathic pain, addiction, and depression.

Dezocine is a well-known compound and described in U.S. Pat. No. 4,605,671, which is incorporated by reference herein in its entirety. Dezocine [(−)-13β-amino-5,6,7,8,9,10,11,12-octahydro-5α-methyl-5,11-methanobenxocyclodecen-31-ol, hydrobromide] is a pale white crystal powder. It has no apparent odor. The salt is soluble at 20 mg/mL, and a 2% solution has a pH of 4.6. Methods of synthesis for dezocine are well known in the art. Any form of dezocine or its derivative, known to one of skilled in the art, can be used for preventing or treating opioid receptor associated diseases or disorders. For example, dezocine of any pharmaceutically acceptable salt, alcohol, hydrate, ester, amide, derivative, analog, polymorph, metabolite, isomer, or prodrug or combination thereof can be used.

This invention may also extend to a dezocine analog, which has a similar pharmacological profile as a partial mu receptor agonist, kappa receptor antagonist, and norepinephrine and serotonin transporter protein inhibitor. For example, a dezocine analog includes dezocine where one or more of the hydrogens on the methyl substituent is replaced with another moiety (e.g., with a halogen or an alkyl group) and has the following structure, where at least one of the R groups is not hydrogen:

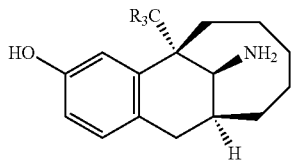

In one aspect, provided herein are pharmaceutical compositions of an opioid, such as dezocine, the compositions comprising: an aqueous solution of dezocine and a cyclodextrin. Preferably, the cyclodextrin is a 2-hydroxypropyl-cyclodextrin, such as 2-hydroxypropyl-β-cyclodextrin (HPBCD) or 2-hydroxypropyl-γ-cyclodextrin (HPGCD). More preferably, the cyclodextrin is 2-hydroxypropyl-γ-cyclodextrin (HPGCD). In some embodiments, the composition is adapted for intravenous administration. In some embodiments, the composition is adapted for oral administration. In some embodiments, the composition is adapted for transmucosal, such as intranasal, administration.

In some embodiments, the HPBCD or HPGCD concentration in the aqueous opioid, such as dezocine, solution is at least 1% (w/v), at least 2.5% (w/v), at least 5% (w/v), at least 7.5% (w/v), at least 10% (w/v), at least 12.5% (w/v), at least 15% (w/v), at least 17.5% (w/v), at least 20% (w/v), at least 22.5% (w/v), or at least 25% (w/v). In some embodiments, the HPBCD or HPGCD concentration in the aqueous opioid, such as dezocine, solution is less than 50% (w/v), less than 45% (w/v), less than 40% (w/v), less than 35% (w/v), less than 30% (w/v), less than 25% (w/v), less than 22.5% (w/v), less than 20% (w/v), less than 17.5% (w/v), less than 15% (w/v). Preferably, the HPBCD or HPGCD has a concentration in the aqueous dezocine solution of about at least 20% (w/v).

In one aspect, the invention relates to opioid nanoparticles, such as dezocine nanoparticles. The size of the nanoparticles may range from about 1 nm to about 200 nm. In one embodiment, the size of the nanoparticles may range from about 5 nm to about 150 nm. In another embodiment, the size of the nanoparticles may range from about 10 nm to about 100 nm. In yet another embodiment, the size of the nanoparticles may range from about 50 nm to about 100 nm. In some embodiments, the size of the nanoparticles is about 1, 5, 10, 20, 30, 50, 80, 100, 150, 200, 500, 600, 700, 800 or 900 nm. In a particular embodiment, the size of the nanoparticles is less than or equal to 100 nm.

In one aspect, the invention relates to opioid microparticles, such as dezocine microparticles. The size of the particles may range from about 1 μm to about 200 μm. In one embodiment, the size of the particles may range from about 5 μm to about 150 μm. In another embodiment, the size of the particles may range from about 10 μm to about 100 μm. In yet another embodiment, the size of the particles may range from about 50 μm to about 100 μm. In some embodiments, the size of the particles is about 1, 5, 10, 20, 30, 50, 80, 100, 150, 200, 500, 600, 700, 800 or 900 μm. In a particular embodiment, the size of the particles is less than or equal to 100 μm.

Opioid nanoparticles or microparticles, such as dezocine nanoparticles or microparticles, can be prepared by a process that comprises the steps of: (a) preparing an opioid, such as dezocine, in solution, (b) preparing a solution comprising poly(vinyl alcohol) (PVOH) and propylene glycol; (c) adding the opioid, such as dezocine, to said solution comprising PVOH and propylene glycol; (d) homogenizing the resulting mixture until forming a nano-emulsion or a micro-emulsion; (e) freezing and thawing said nano-emulsion or micro-emulsion for a predetermined time to produce hydrogel opioid nanoparticles, opioid nanoparticles, hydrogel opioid microparticles, opioid microparticles; (f) filtering said nanoparticles or microparticles; and (g) suspending the opioid nanoparticles or opioid microparticles in solution. In one embodiment, the nanoparticles are filtered through a filter having a pore size of 100 nm.

One or more additional therapeutically effective agent(s) may be conjugated to the dezocine, incorporated into the same composition as the dezocine (e.g., the additional agent(s) is incorporated into the dezocine nanoparticles or microparticles), or may be administered as a separate composition. The other therapeutically agent or treatment may be administered prior to, during and/or after the administration of dezocine.

In one aspect, the invention relates to a composition comprising dezocine in combination with another compound capable of preventing, inhibiting, or reducing an adverse effect associated with dezocine. In a particular embodiment, the other compound is ondansetron. For example, the composition comprises dezocine and ondansetron, wherein dezocine may be present in an amount effective to treat an opioid receptor associated disease or disorder in a subject and ondansetron may be present in an effective amount to reduce a dezocine related adverse effect. Examples of adverse effects include, for example, but are not limited to, nausea and vomiting.

Ondansetron (INN), originally marketed under the brand name Zofran, which is a serotonin 5-HT$_3$ receptor antagonist. Ondansetron is an anti-emetic agent used to prevent nausea and vomiting. Ondansetron is a well-known compound and described in U.S. Pat. Nos. 7,288,660 and 4,695,578, each of which is incorporated by reference herein in its entirety. Methods of synthesis for ondansetron are known in the art. Any form of ondansetron or its derivative, known to one of skilled in the art, can be used. For example, ondansetron of any pharmaceutically acceptable salt, alcohol, hydrate, ester, amide, derivative, analog, polymorph, metabolite, isomer, or prodrug or combination thereof can be used.

The dezocine compositions describe herein can be administered adjunctively with other active agents such as analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastrointestinal drugs, muscle relaxants, nutritional agents, vitamins, parasympathomimetics, stimulants, anorectics and anti-narcoleptics.

Specific examples of compounds that can be adjunctively administered with dezocine include, but are not limited to, aceclofenac, acetaminophen, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, diazepam, dibenzepin, diclofenac sodium, diflunisal, dihydrocodeine, dihydroergotamine, dihydromorphine, dimetacrine, divalproex, tizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, Ginko biloba, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketamine, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an antinarcoleptic), molindone, morphine, morphine, hydrochloride, nabumetone, nadolol, naproxen, naratriptan, nefazodone, neuronatin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, tiospirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The invention further provides methods of preventing or treating a disease or condition. The methods may include the step of administering to a mammal in need thereof a therapeutically effective amount of dezocine, ondansetron, or a combination thereof.

In one embodiment, the invention provides a method for preventing or treating opioid receptor associated diseases, in a subject, the method comprising: administering to said subject a therapeutically effective amount of dezocine or a pharmaceutical composition thereof (e.g., compositions of the dezocine nanoparticles or microparticles described herein). In some embodiments, the method further comprises administering a therapeutically effective amount of ondansetron or a pharmaceutical composition thereof. In some embodiments, opioid receptor associated diseases are treated by administering a pharmaceutical composition (e.g., compositions of the dezocine nanoparticles or microparticles described herein) that comprises a therapeutically effective amount of both dezocine and ondansetron.

An opioid receptor can be a mu opioid receptor, a kappa receptor, a delta opioid receptor, or combinations thereof. In one example, dezocine treats opioid receptor associated disease by interacting with a norepinephrine transporter (NET), a serotonin transporter (SERT), or a combination thereof.

Examples of opioid receptor associated diseases or disorders include, for example, but are not limited to, pain (e.g., neuropathic pain), addiction (e.g., addiction to a substance or a drug, such as heroin or cocaine), and depression.

In some embodiments, methods are provided for preventing or preventing or treating opioid addiction in a subject, the methods comprising: administering to said subject a therapeutically effective amount of dezocine nanoparticles described herein.

The pharmaceutical compositions may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which toxic or detrimental effects of the molecule are outweighed by the therapeutically beneficial effects.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

The compounds and pharmaceutical compositions comprising the same can be administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally, intrathecally, intranasally, and inhalationally.

The pharmaceutical compositions can be administered orally, and thus can be formulated in a form suitable for oral administration, i.e. as a solid or a liquid preparation. Suitable solid oral formulations include, for example, but are not limited to, tablets, capsules, pills, granules, pellets and the like. Suitable liquid oral formulations include, for example, but are not limited to, solutions, suspensions, dispersions, emulsions, oils and the like. In one embodiment of the present invention, the active ingredient is formulated in a capsule. In accordance with this embodiment, the compositions of the present invention comprise, in addition to the active compound and the inert carrier or diluent, a hard gelating capsule.

The pharmaceutical compositions can also be administered by intravenous, intra-arterial, or intra-muscular injection of a liquid preparation. Suitable liquid formulations include, for example, but are not limited to, solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In yet another embodiment, the pharmaceutical compositions are administered intra-muscularly and are thus formulated in a form suitable for intra-muscular administration.

The pharmaceutical compositions can also be administered topically to body surfaces and are thus formulated in a form suitable for topical administration. Topical formulations include, in another embodiment, gels, ointments, creams, lotions, drops and the like.

In one embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In one example, the active compound is delivered in a vesicle, e.g., a liposome.

The compositions of the invention may include carriers or diluents. Examples of such carriers or diluents include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Pharmaceutically acceptable carriers for liquid formulations can be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

Parenteral vehicles (for subcutaneous, intravenous, intra-arterial, or intramuscular injection) may include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from but not limited to milk or eggs.

The compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In some embodiments, the pharmaceutical compositions provided herein are controlled-release compositions, i.e. compositions in which the active compound is released over a period of time after administration. Controlled- or sustained-release compositions include formulation in lipophilic depots (e.g., fatty acids, waxes, oils). In another embodiment, the composition is an immediate-release composition, i.e. a composition in which of the active compound is released immediately after administration.

In one embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g., in microspheres in or an implant. In yet another embodiment, a controlled release system is placed in proximity to the target cell, thus requiring only a fraction of the systemic dose (see, e.g., Goodson, in Medical Applications of Controlled Release, vol. 2, pp. 115-138 (1984); and Langer R, Science 249: 1527-1533 (1990)).

The compositions also include, in another embodiment, incorporation of the active material into or onto particulate preparations of polymeric compounds such as polylactic acid or polylactide (PLA), polyglycolic acid, PLGA or poly(lactic-co-glycolic acid) hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included are particulate compositions coated with polymers (e.g., poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, cyclodextrin, cucurbituril, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In one embodiment, the methods of the present invention comprise administering an active compound as the sole active ingredient. However, also encompassed within the scope of the present invention are methods for preventing or treating diseases and disorders that comprise administering the active compound in combination with one or more therapeutic agents.

The administration of dezocine with other agents and/or treatments may occur simultaneously, or separately, via the same or different route, at the same or different times. Dosage regimens may be adjusted to provide the desired response (e.g., a therapeutic or prophylactic response).

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The compositions of the invention may be administered only once, or it may be administered multiple times or continuous infusion. For multiple dosages, the compositions may be, for example, administered three times a day, twice a day, once a day, once every two days, twice a week, weekly, once every two weeks, or monthly.

Dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to a particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets), intrathecal, and inhaltional. Administration to a host may occur in a single dose or in repeat administrations or continuous infusion, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, e.g., Remington's Pharmaceutical Sciences, Mack Publishing Co.).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

The methods of treatment described herein can be used to treat a suitable mammal, including primates, such as monkeys and humans, horses, cows, cats, dogs, rabbits, and rodents such as rats and mice. Preferably, the mammal to be treated is human.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Novel Molecular Targets of Dezocine and Their Clinical Implications

While dezocine is a partial mu opioid receptor agonist, it is not a controlled substance. Thus, the characterization of the molecular targets of dezocine has significant scientific and clinical implications. The goal of this study is to characterize molecular targets for dezocine and their implications.

A binding screen for dezocine was performed on 44 available receptors and transporter proteins. Functional assays for the novel targets were performed along with computation calculations to locate the binding site. A G protein activation study was performed for the human kappa opioid receptor to determine whether dezocine is a kappa antagonist. Data are presented as mean±SE. The affinities for dezocine were 3.7±0.7 nM for the mu receptor, 527±70 nM for the delta receptor, and 31.9±1.9 nM for the kappa receptor. Dezocine failed to induce G protein activation with kappa opioid receptor and concentration dependently inhibited kappa agonist (salvinorin A and nalbuphine) induced receptor activation, indicating that dezocine is a kappa antagonist. Two novel molecular targets (norepinephrine transporter, NET; and serotonin transporter, SERT) were identified. Dezocine concentration-dependently inhibited norepinephrine and serotonin reuptake in vitro. The half maximal inhibitory concentrations (expressed as pIC50) were 5.68±0.11 for NET and 5.86±0.17 for SERT. Dezocine occupied the binding site for known NET and SERT inhibitors. The unique molecular pharmacological profile of dezocine as a partial mu receptor agonist, a kappa receptor antagonist and a norepinephrine and serotonin reuptake inhibitor (via NET and SERT) was revealed. These discoveries show important clinical implications and drug interactions of dezocine.

Materials and Methods

All chemicals (except those specified otherwise) were obtained from Sigma-Aldrich (St. Louis, Mo.) and were reagent grade or higher. Dezocine was obtained from Yangtze River pharmaceutical group (Taizhou, Jiangsu, China) with 99.9% purity. All chemicals were used without further purification. The chemical structures of the ligands that have the same targets as dezocine and were used for comparison in this study are listed in FIG. 1.

Radioligand Binding Assays and Affinity Determination

A primary binding screen for dezocine was performed on 44 available receptors (mostly GPCRs, see Table 1). Evidence for interaction was based on the inhibition of the reference ligand-binding signal. Dezocine was diluted in standard binding buffer (50 mM Tris-HCl, 10 mM $MgCl_2$, 0.1 mM EDTA, pH 7.4) to a final concentration of 10 μM. Briefly, 50 μL aliquots of radioactive ligand (5 nM) were added to wells of a 96-well plate, which contained 25 μL of the reference or test ligands. We employed transfected cell lines expressing mainly human (unless otherwise specified) recombinant receptors, monoamine transporters, or ion channels for crude membrane preparation. Detailed information about our membrane preparation is well known in the art and can be obtained from publicly available protocol online. Crude membrane fractions containing the receptors were resuspended in standard binding buffer and 50 μL aliquots added to each well. The reactions were incubated at room temperature for 1.5 hours to allow for radioligand binding equilibration. Bound radioactivity was harvested by rapid filtration through a 0.3% polyethyleneimine-treated, 96-well filter mats using a 96-well Filtermate harvester. The dried filters were treated with melted scintillant and a Microbeta scintillation counter was utilized to measure the radioactivity retained on the filter.

The secondary binding assay was performed only when the inhibition in the primary screen was over 50%. A secondary binding assay was utilized to determine the binding affinity for the identified receptor. Dezocine was prepared in standard binding buffer and serially diluted to the desired concentrations.

50 μL aliquots of radioactive ligand (5 nM) were added to wells of a 96-well plate, which contained 25 μL dezocine aliquots. 50 μL of a crude membrane fraction of cells expressing the respective receptors were applied to each well. Reaction incubation, harvesting and radioactivity measurement from the primary assay were repeated. Affinity is expressed as $pK_i$ ($-\log K_i$).

TABLE 1

| Receptor and ion channels screened | |
|---|---|
| Receptor name | Receptor subtypes |
| Serotonin receptors | 5-HT1A, 5-HT1B, 5-HT1D, 5-HT1E, 5-HT2A, 5-HT2B, 5-HT2C, 5-HT3, 5-HT5A, 5-HT6, 5-HT7 |
| Adrenoceptor | alpha 1A, alpha1B, alpha1D, alpha 2A, alpha 2B, alpha 2C, Beta1, Beta2, Beta3 |
| Dopamine receptors | D1, D2, D3, D4, D5 |
| GABA receptors | GABA-A, rat benzodiazepine site |
| Muscarinic receptors | M1, M2, M3, M4, M5 |
| Sigma receptors | Sigma1, Sigma2 |
| Histamine receptors | H1, H2, H3, H4 |
| Biogenic amine transporters | serotonin transporter; norepinephrine transporter; dopamine transporter |
| Opioid receptors | mu receptor; kappa receptor; delta receptor |

All the proteins are from human except Sigma2 and benzodiazepine site that are from rat.
HT, Serotonin receptor;
alpha, alpha adrenergic receptor;
Beta, beta-adrenergic receptor;
D, dopamine receptor;
GABA, gamma-aminobutyric acid receptor;
H, histamine receptor;
M, muscarinic receptor;
Sigma, sigma receptor.

G Protein Activation by Kappa Receptor Treated with Agonists, Partial Agonists and Antagonists Membrane preparations of recombinant human kappa opioid receptor expressed in the mammalian cell line Chem-5 were obtained from Millipore (Billerica, Mass.). The effects of specific kappa opioid receptor ligands on the activation of the recombinant receptor were investigated by measuring G protein activation in vitro. Nalbuphine and salvinorin A (full agonist) and nor-binaltorphimine (antagonist) were utilized as controls.

The assay reports the initial rates of activation of heterotrimeric G proteins (G$\alpha i_{i1}\beta_1\gamma_2$) on an agonist-bound receptor by measuring the accumulation of [$^{35}$S]-GTPγS (non-hydrolyzable analog of GTP) bound to the activated G$\alpha_{i1}$ subunit. Myristoylated G$\alpha_{i1}$ was expressed in *E. coli* and purified as previously described. Recombinant human $\beta_1\gamma_2$ subunits of G protein were expressed in baculovirus-infected Sf9 cells and purified as previously described. The G protein activation assay was conducted as follows (final concentrations in 50 µL reaction mixture are given in parentheses): the membrane sample was diluted into ice-cold 10 mM 3-(N-morpholino)propanesulfonic acid (MOPS) buffer to reach a protein concentration of 40 ng/µL. 10 µL of the diluted dispersion were dispensed into presiliconized glass tubes and mixed with the ligand in MOPS buffer containing 0.1% (w/v) BSA. Upon addition of a mixture of G$_{\alpha i1}$ (100 nM) and G$_{\beta1\gamma2}$ (500 nM), the tubes were incubated on ice for 30 minutes. The reaction was started by addition of MOPS buffer pH=7.5 (50 mM), EDTA (1 mM), MgCl$_2$ (3 mM), GDP (4 µM), BSA (0.3% w/v), NaCl (100 mM), DTT (1 mM), and [$^{35}$S]-GTPγS (5 nM, 1250 Ci/mmol) followed by rapid transfer of the tubes to a water bath at 30° C. The incubation continued for 45 minutes. The reaction was terminated by addition of 2 mL of ice-cold stop solution, TNMg (20 mM Tris-HCl pH=8.0, 100 mM NaCl, and 25 mM MgCl$_2$). The reaction mixture was rapidly filtered through nitrocellulose filters (Millipore). Filters were washed four times with 2 mL each of cold TNMg buffer, dried, placed in scintillation vials filled with ScintiSafe Econo F scintillation liquid (Fisher, Waltham, Mass.), and the radioactivity counted. Duplicate samples corresponding to every ligand concentration point were counted.

To test whether dezocine could antagonize the full agonists, the kappa receptor was preactivated with either nalbuphine (250 nM) or salvinorin A (20 nM), a highly selective non-opioid kappa receptor agonists with strong affinity. The kappa receptor was then treated with increasing concentrations of dezocine.

Norepinephrine Transporter (NET) and Serotonin Transporter (SERT) Reuptake Assay The potency of dezocine as an inhibitor of norepinephrine and serotonin uptake on human cloned NET and SERT, stably expressed in Human Embryonic Kidney 293 cells, was determined using the neurotransmitter assay kit from the Molecular Devices (Sunnyvale, Calif.) as described previously. In brief, Human Embryonic Kidney 293 cells were plated in Poly-L-Lys (PLL) coated 384-well black clear bottom cell culture plates in DMEM+1% dFBS, at a density of 15,000 cells per well in a total volume of 40 µl. The cells were incubated for a minimum of 6 hours before use in the assays. The medium was removed and 20 µL of assay buffer (20 mM HEPES, 1×HBSS, pH 7.40) was added, followed by 5 µL of 5× drug solutions. The plate was incubated at 37° C. for 30 min. After the incubation, 25 µL of dye solution was added and fluorescence intensity was measured after 30 mm at 37° C., using FlexStation II (bottom read mode, Excitation at 440 nm, Emission at 520 nm with 510 nm cut-off) from the Molecular Devices. Results (Relative Fluorescence Unit) were exported and plotted against drug concentrations in Prism 5.02 (GraphPad Software, Inc. La Jolla, Calif.) for nonlinear regression to obtain inhibitory potency. The half maximal inhibitory concentration were determined and expressed as pIC$_{50}$ (pIC$_{50}$=−log (IC$_{50}$)).

Docking Calculations

Docking calculations were carried out using Docking-Server as previously described to locate and visualize the binding site. The coordinates of the crystal structure were obtained from the protein data bank (PDB) with access code 4DKL for murine mu receptor and 4DJH for kappa receptor. The coordinates for the serotonin transporter were taken from the recently published model based on the LeuT 3F3A crystal structure. The coordinates for the norepinephrine transporter were obtained from the recently published model based on the crystal structure (PDB ID code 2A65) of LeuT from *Aquifex aeolicus*. Dezocine docking calculation on a LeuT crystal coupled with desipramine (PDB ID code 2QJU) was also performed to identify the potential overlap of the binding sites. Semi-empirical charges calculated by MOPAC2009 were added to the ligand atoms. Essential hydrogen atoms, Kollman united atom type charges, and solvation parameters were added to the receptor using AutoDock tools provided by the server. Grid maps of 30×30×30 Å grid points with 0.375 Å spacing centered at the known ligand binding site were generated using the Autogrid program. All the ligand searches were performed using the Solis and Wets local search method with a Lamarckian genetic algorithm. Initial position, orientation, and torsions of the ligand molecules were set randomly. The three-dimensional coordinates of the tested compound were obtained from the PubChem database. PyMOL (Version 1.5.0.4, Schrodinger LLC, New York, N.Y.) was used to render the graphics for presentation.

Data Analysis

The data are presented as mean±SE from three repeats. The results were analyzed using GraphPad Prism (version 5.02 Windows version). EC50s are determined using the following model as defined in GraphPad: Y=Bottom+(Top-Bottom)/(1+10^((Log EC50−X)*HillSlope)). Top and Bottom are plateaus in the units of the Y axis. EC50 is the concentration of a ligand that gives a response half way between Bottom and Top. HillSlope describes the steepness of the family of curves.

Results

Interaction with Opioid Receptors

Figure 2:
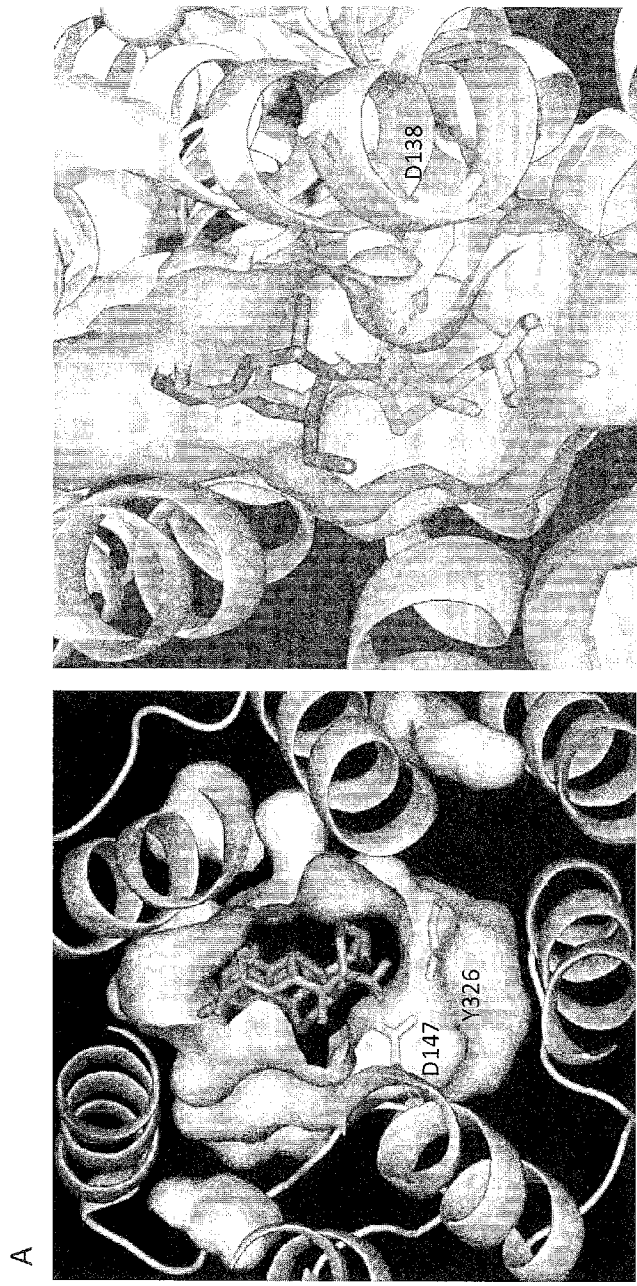
FIG. 2. A) Dezocine (magenta) overlaps with beta-Funaltrexamine (orange) a mu receptor antagonist and the ligand found in the crystal structure of the mu opioid receptor (4DKL), in the binding pocket. Polar interaction with ASP147 and TYR326 is predicted. B) Dezocine (magenta) overlaps with JDTic (orange), a kappa receptor antagonist and the ligand found in the crystal structure of the kappa opioid receptor (4DJH), in the binding pocket. Some of interacting residues (ASP 138, TYR 139 and MET 142) are colored in yellow. A nitrogen in dezocine might hydrogen bond with oxygen atoms of ASP 138 (distance colored in magenta, 2.6 Å, or in green, 2.8 Å).

While dezocine binds to all three major subtypes of opioid receptors (Table 2), it only weakly interacts with the delta receptor. We determined affinities for dezocine as 3.7±0.7 nM for the human mu receptor, 527±70 nM for the human delta receptor, and 31.9±1.9 nM for the human kappa receptor (Table 3). As indicated in FIG. 2, dezocine docks to the known binding site for opioid ligands in both the mu and kappa receptor. Hydrogen bonding with ASP 147 (149 in human mu) contributes to the strong affinity of dezocine to the mu receptor. TYR326 also has polar interaction with dezocine in the mu receptor as demonstrated in FIG. 1A. In the case of the kappa receptor, dezocine hydrogen bonds with ASP 138 as predicted by docking calculations (FIG. 2B).

TABLE 2

Primary binding for the receptors

| Receptors | Dezocine (% inhibition) | Naloxone (% inhibition) |
|---|---|---|
| 5-HT1A | 43.5 | 5.8 |
| 5-HT1B | −14.1 | −1 |
| 5-HT1D | −0.4 | −1.6 |
| 5-HT1E | −2.4 | −5.7 |
| 5-HT2A | −10 | 15.2 |
| 5-HT2B | −11.9 | 49.6 |
| 5-HT2C | 19.8 | 21.1 |
| 5-HT3 | 11.8 | 0 |
| 5-hT5A | 3.4 | 28.9 |
| 5-HT6 | 10.9 | 27.6 |
| 5-HT7 | 20.9 | 60.3 |
| Alpha1A | 4.9 | 4 |
| Alpha1B | 14.7 | −2 |
| Alpha1D | 8.9 | 19.7 |
| Alpha2A | 40.9 | 12.9 |
| Alpha2B | 21.2 | 14.7 |
| Alpha2C | −7.9 | 22.7 |
| Beta1 | 10 | 14.7 |
| Beta2 | −4.5 | −2.6 |
| Beta3 | −15 | −3.1 |
| BZP Rat Brain Site | 11.5 | 22.2 |
| D1 | 11.5 | 5.5 |
| D2 | −3.8 | −0.8 |
| D3 | −9.4 | 1.9 |
| D4 | −5.1 | −5.8 |
| D5 | −6.3 | 2.1 |
| DAT | 15.8 | −12.6 |
| DOR | 58.5 | 99.3 |
| GABAA | −10.1 | −1.1 |
| H1 | 20.7 | 10.8 |
| H2 | 33.6 | 57.4 |
| H3 | −1.6 | 8.9 |
| KOR | 91.3 | 100.5 |
| M1 | −6.8 | 24 |
| M2 | 31.5 | −11.4 |
| M3 | −3.4 | 20.1 |
| M4 | 2.5 | 11 |
| M5 | 19.4 | 32.1 |
| MOR | 89.6 | 99.4 |
| NET | 86.4 | 43.8 |
| SERT | 97.7 | 44 |
| Sigma 1 | 21.7 | 9.6 |
| Sigma 2 | 6.3 | 26.4 |

All the proteins are from human except Sigma2 and benzodiazepine site that are from rat.
5-HT, Serotonin receptor;
alpha, alpha adrenergic receptor;
Beta, beta-adrenergic receptor;
D, dopamine receptor;
DAT, dopamine transporter;
GABA, gamma-aminobutyric acid receptor;
H, histamine receptor;
M, muscarinic receptor;
NET, norepinephrine transporter;
SERT, serotonin transporter;
Sigma, sigma receptor.

TABLE 3

Affinities with major opioid receptors for dezocine

| Ki (nM) | MOR | DOR | KOR |
|---|---|---|---|
| Dezocine | 3.7 ± 0.7 | 527 ± 70 | 31.9 ± 1.9 |
| Naloxone | 6.12 ± 0.4 | 81.4 ± 2.66 | 2.55 ± 0.14 |
| Morphine | 2.8 ± 0.2 | 648.8 ± 59.7 | 55.96 ± 6.99 |

MOR, mu opioid receptor;
DOR, delta opioid receptor;
KOR, kappa opioid receptor

Kappa Receptor Antagonism

Consistent with published data, nalbuphine behaved as a full kappa receptor agonist and fully activated the G protein in the presence of membranes containing kappa receptor as indicated in FIG. 3A. There was no significant G protein activation with dezocine in the presence of kappa receptor, indicating that dezocine acted as an antagonist (FIG. 3A). To confirm this, the G protein was pre-activated with a full agonist (Nalbuphine or Salvinorin A), and then increasing amounts of dezocine were added. As indicated in FIG. 3B, dezocine inhibited the agonist effect concentration-dependently with a total blockage at high concentration. This finding correlated the lack of G protein activation observed in FIG. 3A. The $IC_{50}$ (T=30° C.) values of inhibition were in a high nanomolar range (~350 nM for competition with nalbuphine or ~800 nM for competition with salvinorin A), indicating that dezocine binds to the receptor at the same site as these full agonists. Interestingly, based on this G protein activation study, nor-binaltorphimine acted as an inverse kappa agonist.

Amine Transporter Proteins as Novel Targets of Dezocine

Figure 4:
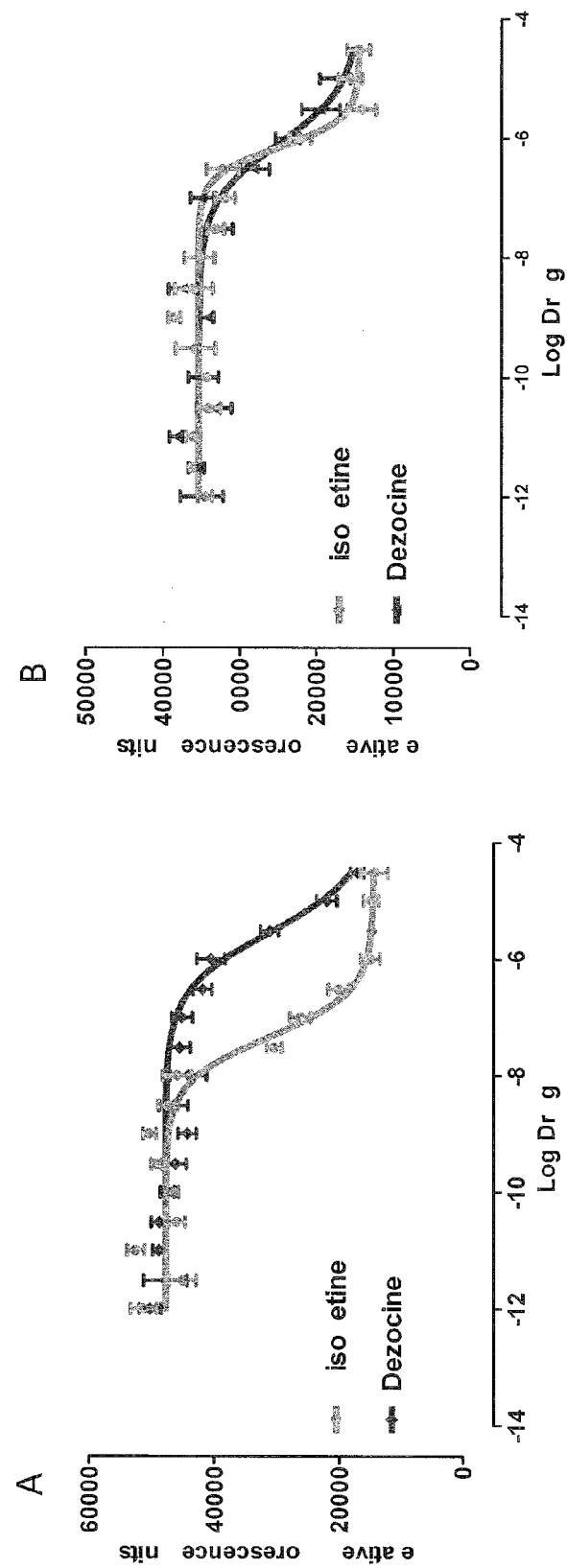
FIG. 4. A) Norepinephrine reuptake is dose dependently inhibited by both dezocine and nisoxetine. However, inhibition is weaker in the case of dezocine. B) Serotonin reuptake is concentration dependently inhibited in the presence of dezocine and nisoxetine with comparable potency. The relationship is plotted using the following model: Y=Bottom+(Top-Bottom)/(1+10^((Log EC$_{50}$-X)*HillSlope)).

As indicated in Table 2, in addition to binding to the opioid receptor, dezocine also inhibits the norepinephrine transporter (NET) with $pK_i$ of 6.00±0.10 and the serotonin transporter (SERT) with $pK_i$ of 6.96±0.08. These interactions were further confirmed by norepinephrine and serotonin reuptake studies. The $pIC_{50}$s at NET were 7.57±0.23 for nisoxetine (positive control) and 5.68±0.11 for dezocine (FIG. 4A). The $pIC_{50}$s of SERT were 5.99±0.07 for nisoxetine and 5.86±0.17 for dezocine (FIG. 4B).

Binding site location in NET and SERT

Figure 5:
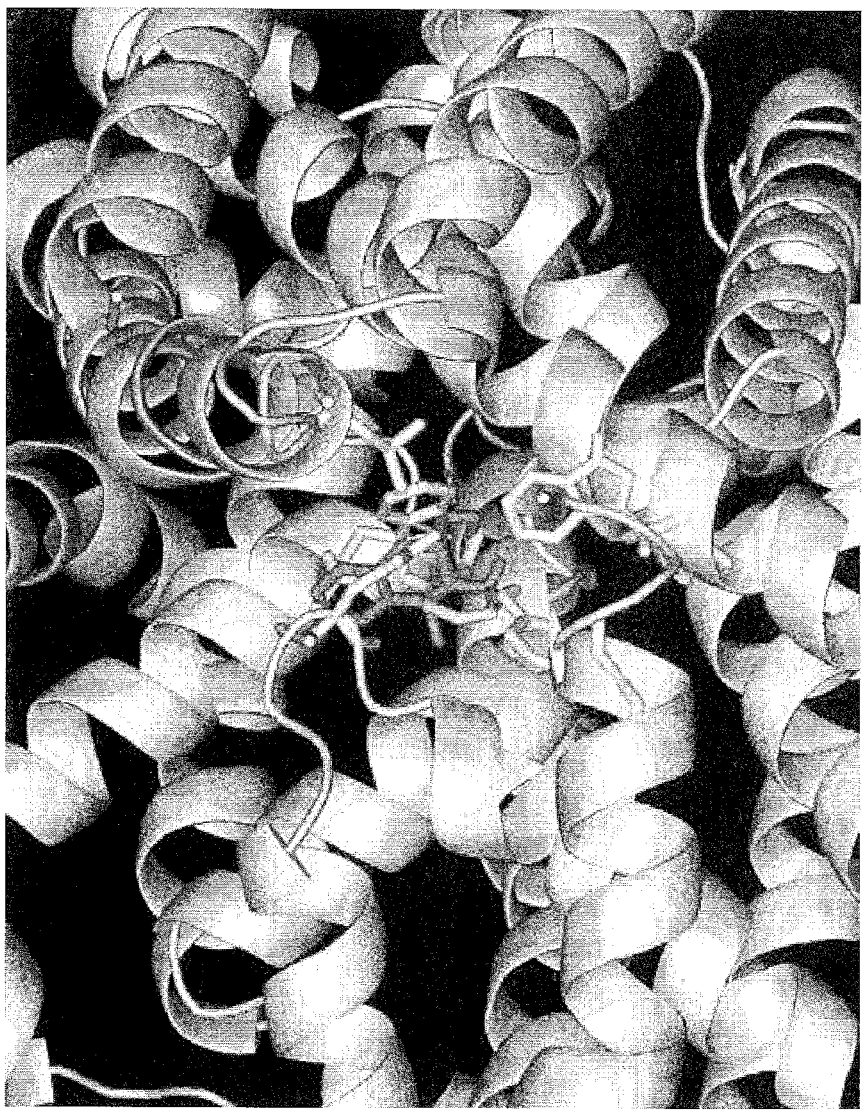
FIG. 5. Docking result of dezocine and nisoxetine in the model of norepinephrine transporter (NET). Dezocine (magenta) shares the same binding site of nisoxetine (cyan), a NET inhibitor, as indicated by the close overlap. Dezocine is located in close proximity to TRP103, TYR127, GLU281, and LEU368 which are all colored in yellow.
Figure 6:
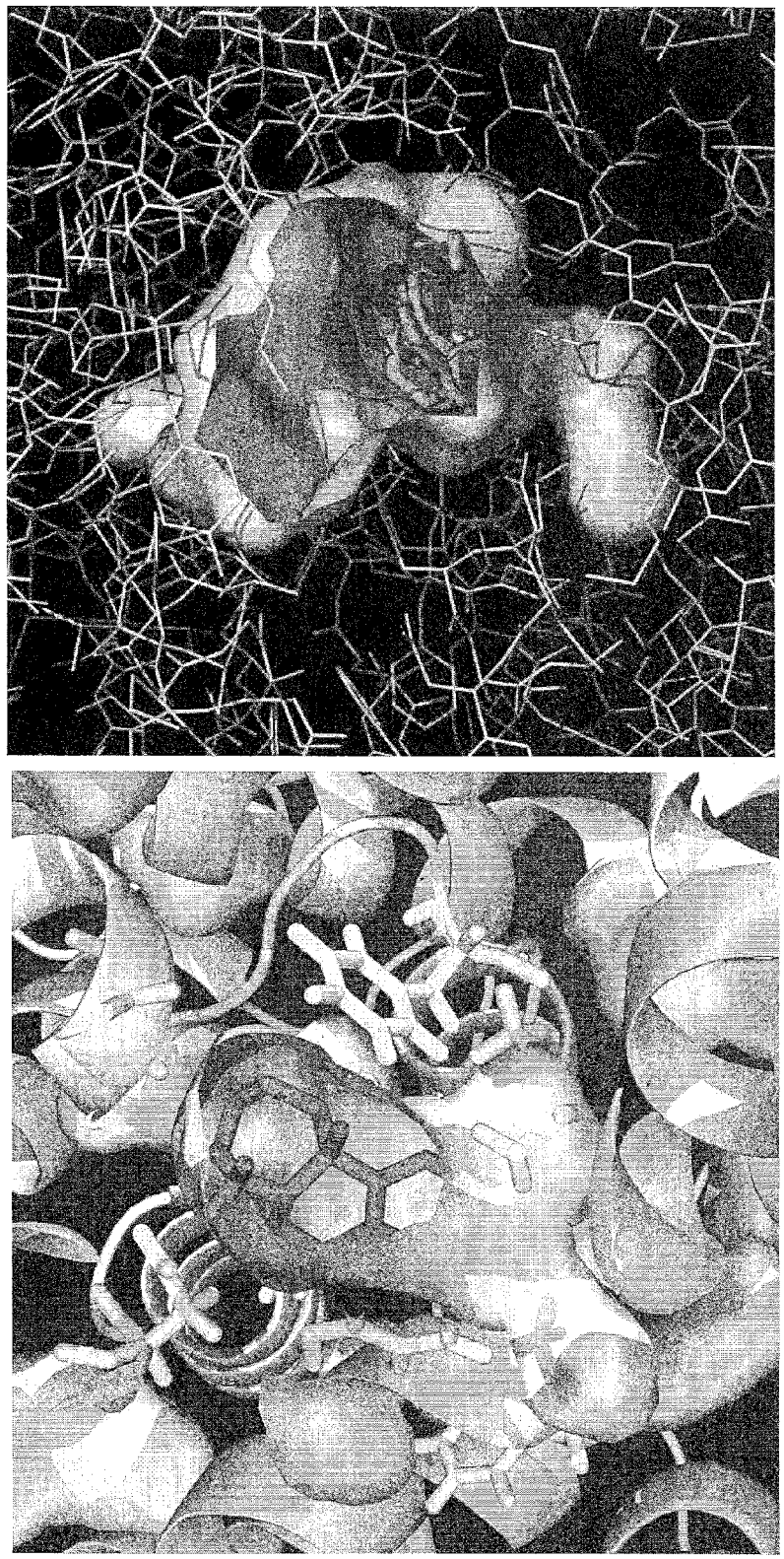
FIG. 6. A) Dezocine (magenta) sits in the preformed ligand binding pocket for selective serotonin reuptake inhibitors in the model of human serotonin transporter. The key interacting residues lining the pocket (Y95, D98, I172, Y176, F335, F341, and S438) are colored in yellow. This binding pocket has been demonstrated to be the binding site for many important clinical drugs such as fluoxetine, sertraline, and amitriptyline. B) Dezocine (magenta) shares the same binding pocket and overlap well with desiprimine (orange), the ligand in the LeuT crystal structure (2QJU).

Consistent with the competitive binding assay, dezocine is predicted to share the same binding site with nisoxetine in the norepinephrine transporter as indicated in FIG. 5. Dezocine is located in close proximity to TRP103, TYR127, GLU281, and LEU368 and might form hydrogen bonds with these residues. Based on the docking prediction shown in FIG. 6A, dezocine binds to the preformed ligand-binding pocket in the model of human serotonin transporter. This pocket has been demonstrated to be the binding site for many selective serotonin reuptake inhibitors including fluoxetine, citalopram, sertraline, fluvoxamine and tricyclic antidepressants such as amitriptyline, desipramine, and imipramine Mutation of the residues lining this pocket (Y95, D98, I172, Y176, F335, F341 and S438) changed the binding capability of these ligands significantly. Dezocine shares the same binding site for desipramine found in the crystal structure of LeuT as indicated in FIG. 6B. Both findings indicate that dezocine may share the same site as selective serotonin reuptake inhibitors or tricyclic antidepressants.

This study details the discovery of the pharmacological interactions of dezocine with the human NET and SERT proteins as well as the molecular characterization of these interactions. This study also confirms the interaction of dezocine with three opioid receptors with different affinities and verifies that dezocine acts as an antagonist of the kappa receptor rather than as an agonist. Collectively, these findings have significant implications, as they help elucidate the mechanisms underlying dezocine's pharmacological effects and present evidence supporting the compound's potential novel clinical applications.

Buprenorphine, a partial mu agonist and kappa antagonist, has been successfully used for addiction treatment for many years with the outcome equivalent to methadone therapy. However, buprenorphine itself is an addictive Schedule III medication and its chronic use creates significant difficulty for optimal perioperative pain management due to its high affinity to the receptor and long half-life Similar to buprenorphine, dezocine is also a partial mu agonist and a kappa antagonist based on our current findings. Its shorter half-life allows for easier titration to an optimal effect as well as rapid removal when full agonism is required during the perioperative period.

Dezocine interacts with NET and inhibits the norepinephrine reuptake. The competitive binding assay and the computational docking calculation suggest that dezocine interacts with NET directly at the binding site for the intrinsic NET ligand One of the striking findings of this study is that dezocine interacts with SERT at its ligand binding site and that serotonin reuptake can be inhibited concentration-dependently by dezocine.

In conclusion, this study explored the interaction of dezocine with three major opioid receptors, demonstrated that dezocine is a kappa antagonist, and its potential use for addiction treatment. Through molecular target profiling, we discovered two novel molecular targets of dezocine in vitro: NET and SERT. The binding sites were characterized using available structural models and docking experiments. Dezocine concentration-dependently inhibited norepinephrine and serotonin reuptake in vitro. These findings show the use of dezocine as a novel medication for the simultaneous treatment of pain and depression.

Example 2

The Anti-Nociception Effect of Dezocine in a Rat Neuropathic Pain Model

The treatment of neuropathic pain (NP) currently remains clinically challenging. In an attempt to identify novel targets of known opioids, we found that dezocine, a non-addictive opioid, inhibits norepinephrine and serotonin reuptake through their transporter proteins which open the potential for dezocine to manage NP. In the present study, the effect of dezocine on NP was observed in a rat model of chronic constriction injury (CCI). The paw withdrawal latency (PWL) and paw withdrawal threshold (PWT) were used to evaluate thermal hyperalgesia and mechanic allodynia for nociceptive response. PWL and PWT tests were performed at 11:00 AM starting from 1 day before CCI surgery and 1, 3, 7, 10 days after right sciatic nerve ligation in the presence or absence of daily intraperitoneal injection of dezocine. The results demonstrated that the CCI-induced thermal and mechanical pain hypersensitivity was attenuated by dezocine significantly and persistently without sign of tolerance, indicating that dezocine could be an alternative medication for the treatment of NP.

Materials and Methods

Pharmaceutical grade dezocine (5 mg/1 mL) and sodium pentobarbital were used in this study.

Animals

The National Institute of Health guidelines for Ethical Conduct in the Care and Use of Animals were strictly followed the experimental protocol approved by the institutional review Committee of Experimental Animal Care. Male Sprague-Dawley rats (Age: 10-12 week, Weight: 200-250 g, from Shanghai Experimental Animal Center of Chinese Academy of Sciences) were housed in a specific pathogen free (SPF) environment with a 12/12 hour light/dark cycle.

Chronic Constriction Injury (CCI) Model

CCI procedures on the sciatic nerve of male SD rats were performed as previously described. Briefly, after rats were anesthetized by i.p. injection of sodium pentobarbital (40 mg/kg), the right sciatic nerve of the mid-thigh level was exposed. Chromic gut 4-0 was loosely tied around the nerve for 4 ligatures with about 1 mm between knots. The ligation was performed to just barely reduce the diameter of sciatic nerve. The ligatures caused intraneural edema and resulted in constriction of nerve. In the sham group, the sciatic nerve was exposed without ligation. The incisions of rats were closed in layers. After recovery from anesthesia, rats were housed individually in the clear plastic cages with soft bedding covered with 3-6 cm of sawdust.

Experimental Protocol

Rats were randomly assigned to three groups (6 rats in each group): a sham group (IP normal saline, IP NS), an NS group (CCI+ IP NS) and a Dezocine group (CCI+ IP dezocine). In the dezocine group, rats of CCI model received intraperitoneal (IP) injection of 3 mg/kg (in 2 ml of volume) body weight of dezocine at 9:00 AM per day starting for the day of the surgery. Same volume of normal saline (2 ml) was injected in the other two groups at the same time.

Evaluation of Thermal Hyperalgesia

The paw withdrawal latency (PWL) to radiant heat was used to evaluate thermal hyperalgesia for nociceptive response as previously described. Rats were placed in transparent plexiglass cage (23×18×13 cm) with a piece of 3-mm-thick glass floor and received heat radiation after acclimating to the environments for 30 minutes. The radiant heat source consists of a high-intensity projection lamp bulb (8V, 50 W), which was located 40 mm below the glass floor beneath the right hind paw of the rats. The heat source projected through a 5×10-mm aperture on the top of a movable case. A digital timer automatically measured the duration between the starting of heat and the paw withdrawal, which was considered as the PWL. The PWL was measured in 0.1 second and a maximum of 20 seconds exposure to radiation was set to avoid injury. Three repeated measurements were performed in each rat with a 5-minute interval between each measurement. PWL tests were performed at 11:00 AM starting from 1 day before CCI surgery and 1, 3, 7, 10 days after surgery.

Evaluation of Tactile Allodynia

The paw withdrawal threshold (PWT) was used to evaluate mechanical allodynia for nociceptive response with Von Frey filaments. The rats were placed in transparent plexiglass cage with a wire mesh floor. After acclimating to their environments for 30 minutes, each filament was applied perpendicularly to the plantar surface of the right hind paw. The end point was determined as paw withdrawal accompanied by biting, head turning and/or licking. The force (in gram, g) needed for this reaction was recorded. The PWT was taken though increasing and decreasing the stimulus strength sequentially with the 'up-and-down' method as described by Chaplan Similar to PWL test, PWT tests were performed at 1 day before and 1, 3, 7, 10 days after CCI surgery.

Statistical Analysis

All data were presented as mean±SEM. Statistical analysis was performed using one-way ANOVA via GraphPad Prism5 software (GraphPad Software Inc, CA, USA). $P<0.05$ was considered statistically significant.

Results

Figure 7:
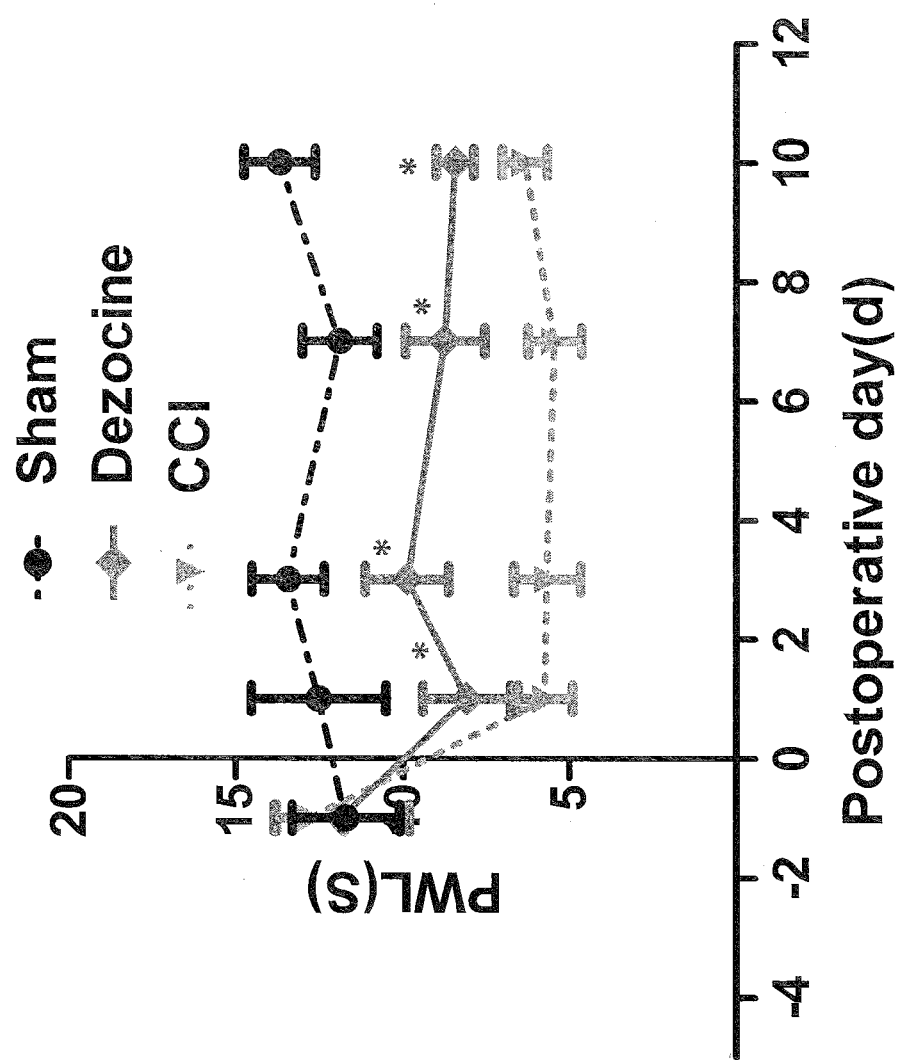
FIG. 7. Changes of paw withdrawal latency (PWL) after injection of dezocine on CCI rats. Rats were administered with dezocine one day before CCI, and then PWL was measured. Following administration of dezocine, PWL was significantly increased comparing to that in the NS group (*P<0.05).

After surgery, the PWL, representing the threshold of thermal hyperalgesia, decreased significantly compared to sham group. Statistically significant difference was found between the NS group and the sham group on 1, 3, 7, 10 days after CCI surgery ($P<0.05$, FIG. 7). Comparing to NS group, after dezocine administration, PWL significantly improved in the dezocine group lasting for 10 days without signs of fluctuation ($P<0.05$), suggesting that dezocine could attenuate thermal hyperalgesia during the whole experimental period without signs of tolerance.

Figure 8:
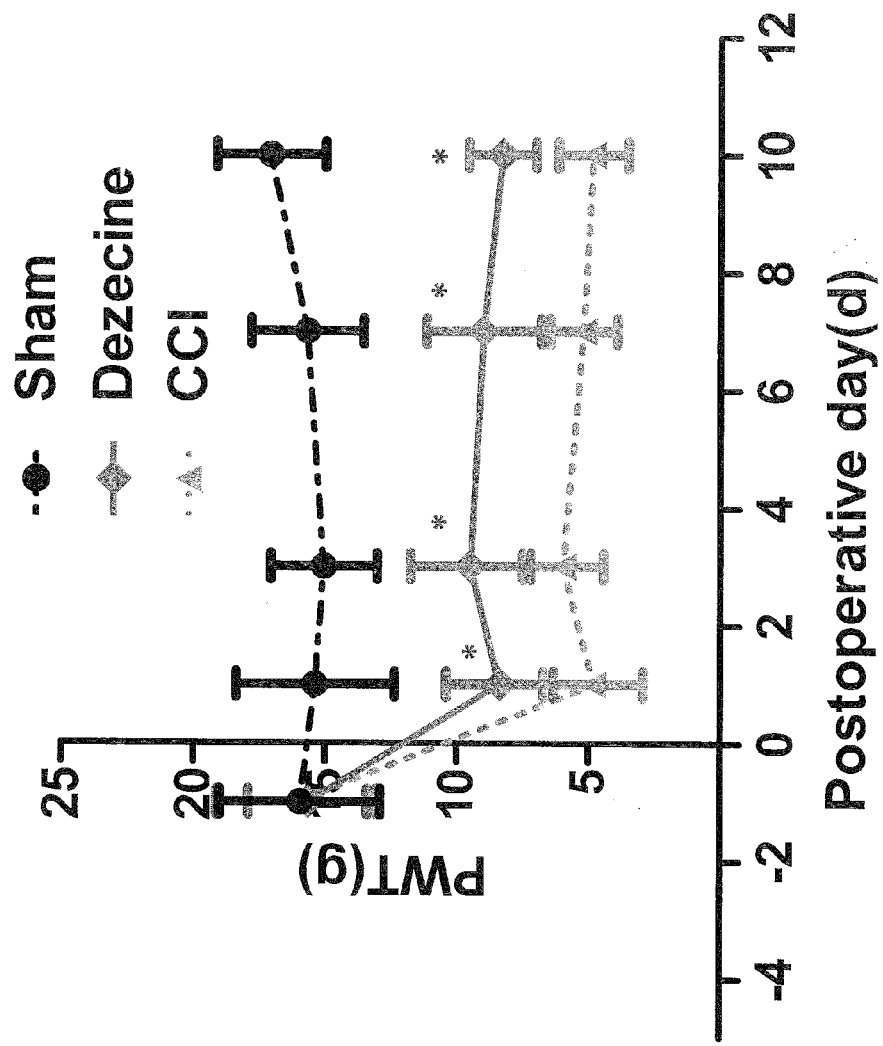
FIG. 8. Changes of paw withdrawal threshold (PWT) after injection of dezocine on CCI rats. PWT was monitored one day before CCI and 1, 3, 7, and 10 day after surgery. At the $1^{st}$, $3^{rd}$, $7^{th}$ and $10^{th}$ day, PWT showed markedly increased comparing to that in the NS group (*P<0.05).

PWT was utilized to measure mechanical allodynia. Mechanical allodynia was induced by CCI, as evidenced by the reduction of PWT (FIG. 8). CCI rats receiving intraperitoneal injection of dezocine, PWT was increased markedly in the dezocine group comparing to the NS group (P<0.05), which suggested an attenuation of allodynia by dezocine (FIG. 8). Similar to PWL, the improvement of PWT was found during the entire experiment period. Taken together, the anti-nociception effect by dezocine started immediately after administration and lasted for 10 days without signs of tolerance.

In the present study, the effect of dezocine on NP was investigated in a rat CCI model. The results indicated that dezocine significantly attenuated the CCI-induced thermal and mechanical pain hypersensitivity, indicating that dezocine could be an alternative medication for the treatment of NP. This clinical indication for dezocine is enormous due to lack to good medication for NP management.

Based on the role of NET and SERT in NP and our previous founding that NET and SERT are new targets of dezocine, we find that the anti-nociception effect of dezocine can be through the inhibition of norepinephrine and serotonin reuptake. Thus, dezocine can be used for NP treatment through opioid system and norepinephrine/serotonin system.

In summary, dezocine significantly attenuated the nociception effect in a neuropathic pain model in rats; indicating that dezocine could be an alternative medication for neuropathic pain management.

Example 3

Dezocine/Ondansetron Composition for Pain Management

This invention relates to a combination of two clinical medications (dezocine and ondansetron) for pain management Similar to buprenorphine, dezocine is an opioid receptor partial agonist, and has the equivalent potency and similar pharmacokinetic profile as that of morphine and has been used for pain management in clinical practice since the 1970s. As a non-DEA controlled medication, the usage of dezocine can therefore reduce the prevalence of opioid addiction.

Figure 9:
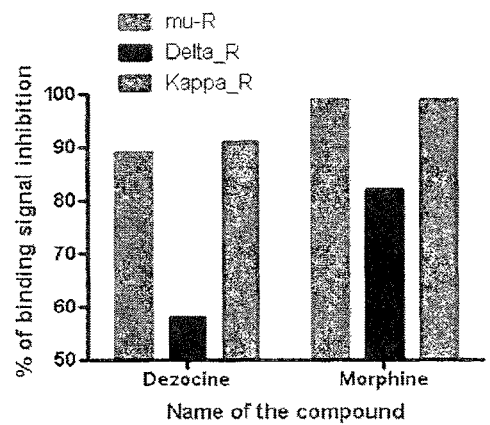
FIG. 9. Relative affinities of dezocine with three opioid receptors as compared with morphine, a classic opioid receptor agonist to all three receptors. Mu-R: mu opioid receptor; Delta-R: delta opioid receptor; kappa_R: kappa opioid receptor.

Dezocine and ondansetron are both FDA approved medication for different clinical indications. Consistent with reported data, dezocine has affinity with all three opioid receptors. It has comparable affinity to mu opioid receptor and kappa receptor with morphine, however, it has much weaker affinity with delta opioid receptor as indicated in FIG. 9.

Figure 10:
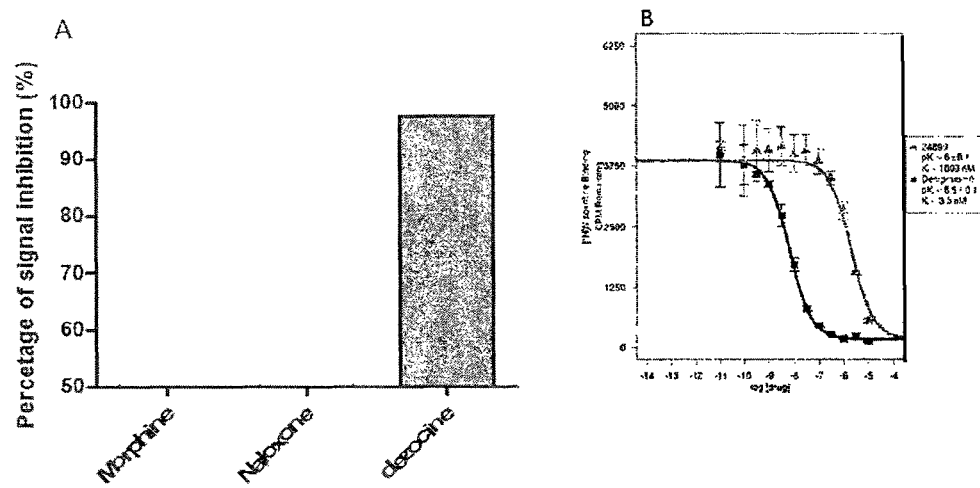
FIG. 10. A: The interaction of dezocine with Norepinephrine Transporter (NET) as compared with morphine and Naloxone. No significant binding activity for morphine and Naloxone is observed. NET plays very important role in pain regulation and is a novel target for pain management. B: The affinity of dezocine with NET (ki=1 μM) as compared with classic NET ligand, desipramine.

Besides the analgesic properties of dezocine through opioid receptors, novel analgesic mechanism of the dezocine has been revealed by screening dezocine agonist currently available protein receptors. Dezocine is not only a mu opioid receptor partial agonist, but it also interacts with norephinephrine transporter (NET) protein, an important pathway for pain regulation as indicated in FIG. 10.

Figure 11:
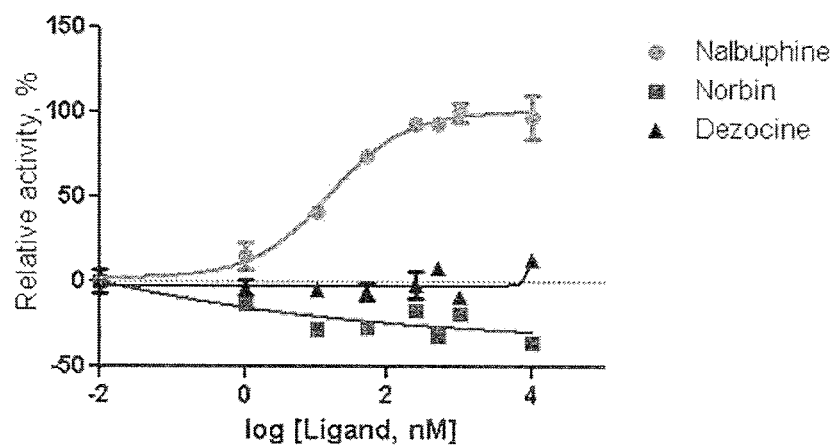
FIG. 11. G-protein activation test for dezocine is compared to nalbuphine, a known kappa receptor agonist, and to norbinortorphmine (Norbin), a known kappa receptor antagonist. Both Norbin and dezocine did not induce G protein activation. This data demonstrate that dezocine is a kappa receptor antagonist.

We recently confirmed that dezocine is a kappa antagonist, rather than a kappa receptor agonist as initially reported. This is a finding explains the lack of addiction reported with clinical usage of dezocine. As indicated in FIG. 11, dezocine did not cause any G protein activation for human kappa receptor. We used nalbuphine as a positive control which is a kappa receptor agonist and induced G protein activation.

The use of dezocine has several advantages. For example, dezocine is not a DEA controlled medication and has no reported addiction to date. All the other commonly used clinical opioids for either pain management or addiction treatment are DEA controlled medications and have addictive properties. In addition, all the other opioids are associated with death. No death reports have been associated with dezocine to date.

Buprenorphine has a very long half-life, which makes it difficult to be titrated for optimal management and difficult to rescue during overdose. Although naloxone has been added into the composition for buprenorphine, the half-life time for naloxone is short relative to buprenorphine. Therefore, the combination of these two compounds results is a poor pharmacological match. The pharmacokinetic profile of dezocine matches well with naloxone.

Furthermore, dezocine has a ceiling effect on respiratory depression. Dezocine is also a mu opioid receptor partial antagonist, which ensures a better side-effect profile than other full opioid receptor agonists. It is also a kappa antagonist, giving it the potential to treat opioid addiction.

Additionally, the analgesic effects of dezocine are not only through opioid receptor, but also via NET protein, which is important for pain regulations. Thus, dezocine could be an effective therapeutics for neuropathic pain.

The combination usage of ondansetron may prevent the most common side effects related to dezocine: nausea and vomiting, a common side effect from most of opioid medication.

Example 4

Dezocine/Ondansetron Compositions for Addiction Treatment

This invention relates to a combination of current clinical medications (dezocine with ondansetron) for addiction management. As discussed above, dezocine has the equivalent potency and similar pharmacokinetic profile of morphine and has been used in clinical practice for pain management since 1970s Similar to buprenorphine, dezocine is also a kappa antagonist and should have the property to treat opioid addiction as buprenorphine has. It is not a DEA controlled medication. Thus, the usage of dezocine can reduce the prevalence of opioid addiction. Adding ondansetron will prevent the most common dezocine-related nausea and vomiting.

As discussed above, dezocine and ondansetron are both FDA approved medication for different clinical indications.

As discussed above, consistent with reported data, dezocine has affinity with all three opioid receptors. It has comparable affinity to mu opioid receptor and kappa receptor with morphine, however, it has much weaker affinity with delta opioid receptor as indicated in FIG. 9. As discussed above, we recently confirmed that dezocine is a kappa antagonist, rather than a kappa receptor agonist as initially reported.

This finding indicates that dezocine can have anti-addiction properties and can be used for addiction treatment.

As indicated in FIG. 11, dezocine did not cause any G protein activation for human kappa receptor. We used nalbuphine as a positive control which is a kappa receptor agonist and induced G protein activation.

Example 5

Dezocine for Addiction Management

There is no optimal therapeutic to manage opioid withdrawal syndrome yet. In the present study, the effect of dezocine on morphine withdrawal syndrome was observed in a rat model. Daily intraperitoneal injection of dezocine markedly reduced morphine withdrawal syndrome, showing that dezocine could be a novel therapeutic strategy for opioid dependent subjects.

Materials and Methods

Animals

All animal experiments were carried out under the guidelines issued by University of Pennsylvania, and conformed to the National Institute of Health guidelines on the ethical use of animals. The experimental protocol was approved by the institutional review committee of University of Pennsylvania. Male Sprague-Dawley rats (Weight: 200-250 g, Age: 10-12 weeks from Shanghai Experimental Animal Center of Chinese Academy of Sciences) were housed in a pathogen free condition with a 12:12 hour light/dark cycle. The room and cage conditions were monitored twice a day. Monitoring for health problems were performed three times a day and all were found healthy during the course of the study.

Animal Model and Protocol

The morphine dependent model was constructed by subcutaneous administration of daily ascending doses of morphine three times/day for 6 consecutive days (5, 10, 20, 40, 50, 60 mg/kg) in all animals except these in the naïve group. (1) The same volumes of normal saline (NS) were received subcutaneously in the naïve group. All other interventional drugs are administered by intraperitoneal injection. Rats were randomly assigned to three groups (15 rats in each group): a naïve group (no morphine will be administered), a normal saline (NS) group (morphine+NS), and a Dez (dezocine) group (morphine+dezocine 5 mg/kg).

Scoring the Symptoms of Morphine Withdrawal Syndrome

On the 1st, 2nd, 3rd, 4th, 5th, 6th and 7th day, 30 mm after intraperitoneal injection of dezocine in the Dez group or normal saline in the control and naïve groups, naloxone (2 mg/kg) is administered to reduce morphine withdrawal syndrome. The symptoms of morphine withdrawal syndrome in each animal were observed for 30 mm after naloxone injection. The scores of withdrawal symptoms were determined according to Maldonado's modified method as described in our previous work (Table 4).

TABLE 4

Scores of morphine withdrawal symptoms (30 min observation time)

| Symptoms | Scores | | |
| --- | --- | --- | --- |
|  | 1 | 2 | 3 |
| wet dog shakes | 1-3 times | 4-6 times | ≥7 times |
| Writhing | 1-3 times | 4-6 times | ≥7 times |
| teeth chattering | 1-3 times | 4-6 times | ≥7 times |
| Jumping | 1-3 times | 4-6 times | ≥7 times |
| Rearing | 1-3 times | 4-6 times | ≥7 times |
| body grooming | 1-3 times | 4-6 times | ≥7 times |
| Ptosis | 1-4 times | 5-8 times | ≥9 times |

Results

Figure 14:
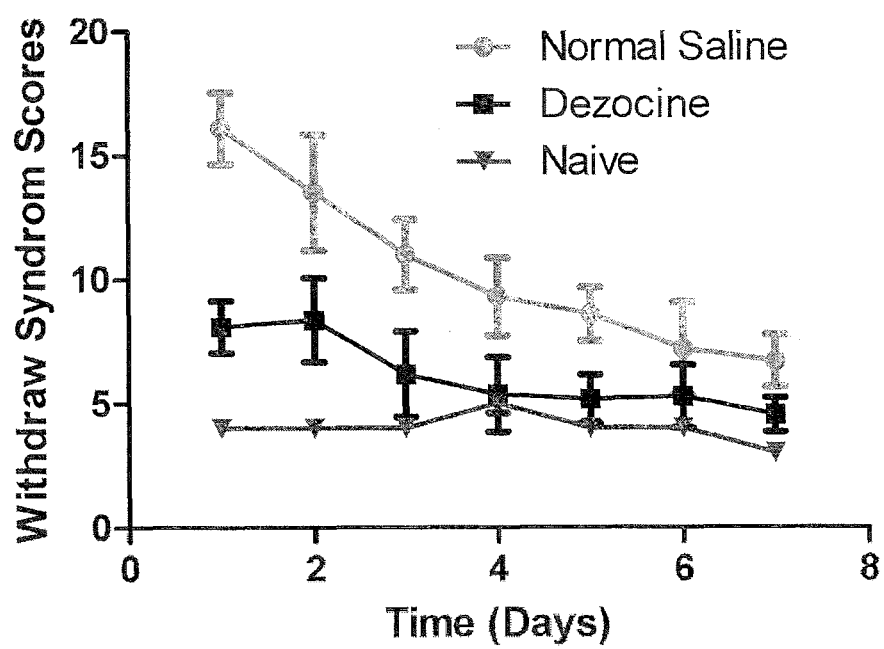
FIG. 14. Total score of morphine withdrawal symptoms. The score of withdrawal symptoms significantly reduced with dezocine treatment. N=8 per group; P<0.01.
Figure 15:
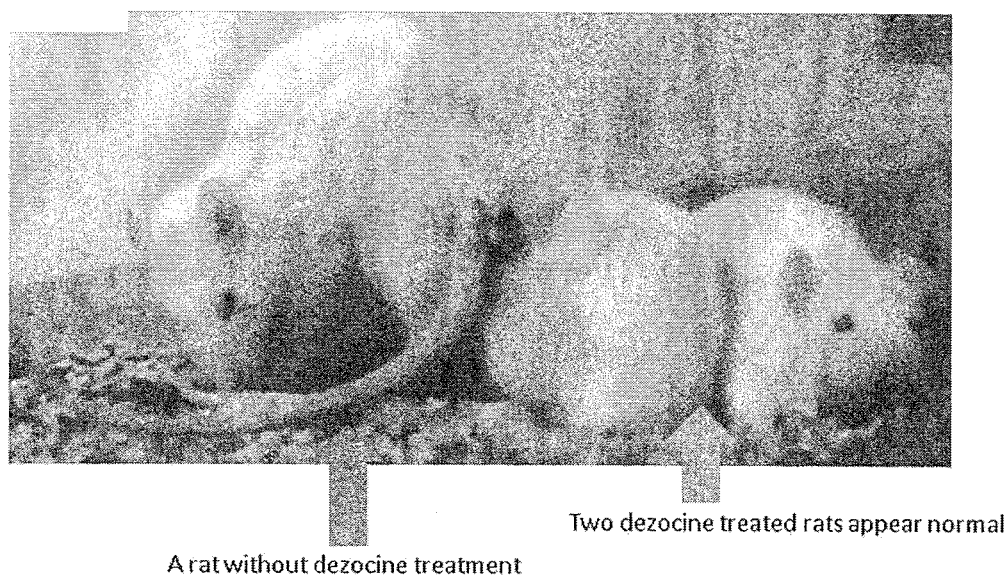
FIG. 15. Writhing and ptosis in the untreated rat (left rat). Such symptoms are not observed in the two rats on the right treated with dezocine.

Compared to the naive group, the scores of the symptoms of morphine withdrawal syndrome were significantly higher after cessation of morphine ($P<0.01$). On the 1st, 2nd, 3rd, 4th, 5th, 6th and 7th day after injection, withdrawal scores decreased significantly in the Dez group compared to the NS groups ($P<0.01$) as shown in FIG. 14. The data indicated that dezocine alleviated the morphine withdrawal syndrome in morphine dependent rats. FIG. 15 indicates that withering and ptosis in a morphine dependent rat, such symptom is not observed in two of the rats treated with dezocine.

Figure 18:
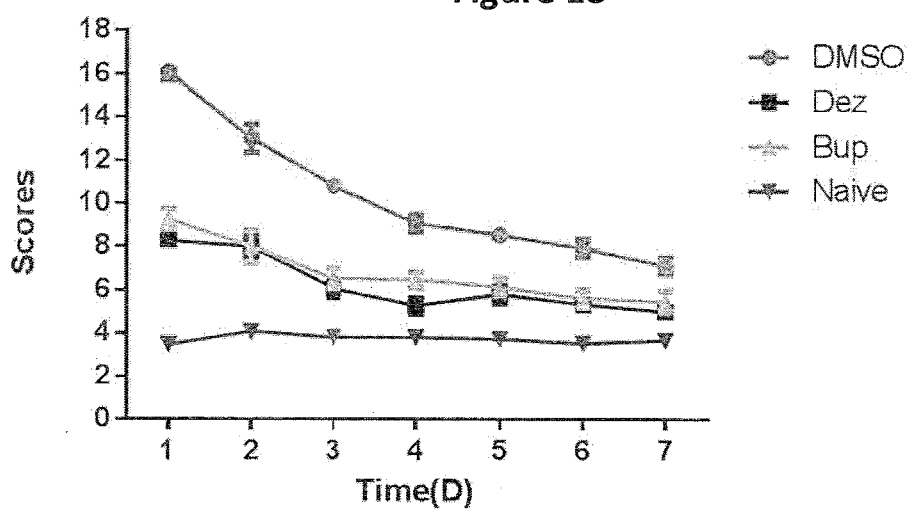
FIG. 18. Total score of morphine withdrawal symptoms. Compared to the naive group, the scores of the symptoms of morphine withdrawal syndrome in DMSO group were significantly higher after cessation of morphine (P<0.01). On the 1st, 2nd, 3rd, 4th, 5th, 6th and 7th day after injection, withdrawal scores decreased significantly in the Dez group and Bup group compared to the DMSO groups (n=12 each group; P<0.01). There was no significantly difference in the scores between the Dez group and the Bup group (P>0.05). The data indicated that dezocine and buprenorphine alleviated the morphine withdrawal syndrome in morphine dependent rats. Dez: dezocine; Bup: Buprenorphine; D: days.

Opioid dependence continues to be a major public health issue. Based on our recent discovery of the unique pharmacological profile of dezocine as a non-addictive opioid, a partial mu agonist and kappa antagonist, similar to that of buprenorphine, we hypothesized that dezocine could be used to manage opioid dependence. In this study, the effects of dezocine and buprenorphine on morphine withdrawal syndrome were compared in a rat morphine dependence model. Daily intraperitoneal injection of dezocine markedly reduced morphine withdrawal syndrome similar to that of buprenorphine (FIG. 18). Astrocyte activation in nucleus accumbens after opioid exposure was observed in the morphine dependent rats, and such astrocyte activation was significantly inhibited in the presence of dezocine and buprenorphine. The molecular target profiling for both dezocine and buprenorphine was performed. Dezocine interact with sigma 1 receptor, while buprenorphine has no interaction with sigma 1 receptor. These findings suggested that dezocine could be an alternative medication for opioid addiction management similar to that of buprenorphine. The advantage of dezocine over buprenorphine for opioid dependence management is proposed.

In sum, dezocine shows a significant reduction of morphine withdrawal syndrome in a morphine dependent rat model, indicating its important therapeutic role in opioid dependent subjects.

Example 6

Dezocine Composition for Depression Disorder

Patients with chronic pain frequently report depression, a condition associated with higher pain intensity and greater prevalence of chronic opioid therapy. Identifying, preventing, and treating depression symptoms in chronic pain patients are essential for reducing co-morbidity and disability. 80% of patients with major depression without psychotic features have painful physical symptoms. Opioids are the main class of medications used to manage moderate and severe pain; however, in addition to addiction, depression is the most notorious side effects of opioid treatment. Consequently, there is a significant medical impetus for developing medications that simultaneously target pain and depression effectively.

While profiling known opioids for novel molecular targets, we discovered that dezocine, a mu opioid receptor partial agonist approved by the FDA for perioperative acute pain management (IV form only), binds strongly with both the norepinephrine transporter (NET) and serotonin transporter (SERT), two of the major cellular targets for antidepressant drugs. Further study indicates that dezocine is a kappa opioid receptor antagonist, explaining why there is no abuse liability related to dezocine so far and it is not listed as a DEA controlled substance. These discoveries show the use of dezocine as a medication to treat depression especially for patients with chronic pain complicated with depression, benefiting millions of patients with chronic pain and depression.

As discussed above, dezocine is a FDA approved medication for different clinical indications. Consistent with reported data, dezocine has affinity for all three opioid receptors. It has comparable affinity to mu opioid receptor and kappa receptor with morphine, however, it has much weaker affinity with delta opioid receptor as indicated in FIG. 9.

We recently confirmed that dezocine is a kappa antagonist, rather than a kappa receptor agonist as initially reported. This finding explains the lack of addiction reported with clinical usage of dezocine. As indicated in FIG. 11, dezocine did not cause any G protein activation for human kappa receptor. We used nalbuphine as a positive control which is a kappa receptor agonist and induced G protein activation.

Figure 12:
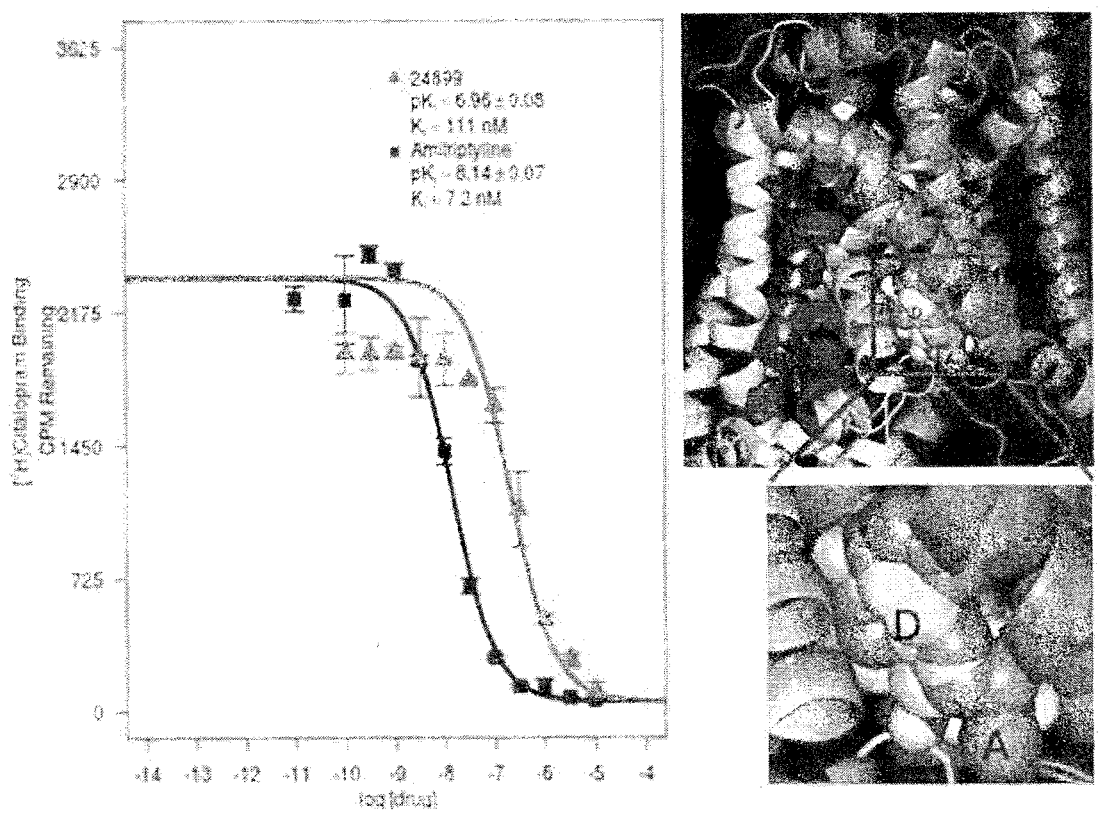
FIG. 12. Left panel: the affinity determination of dezocine (24899, 111 nM) as compared with amitriptyline, a clinical antidepressant which interacts with SERT. Right panel: the binding site of dezocine (D) in SERT overlaps well with amitriptyline (A).

After screening known opioid compounds for novel targets, we discovered that dezocine interacts with both the norepinephrine transporter (NET) and serotonin transporter (SERT). The interaction of dezocine with both NET and SERT indicates that it can have antidepressant properties. The affinity and binding site of dezocine for SERT are indicated in FIG. 12, while the affinity and binding site of dezocine for NET are indicated in FIG. 13.

Example 7

Dezocine and Depression

In this study, we used a forced swim test to explore whether dezocine has anti-depressive effect as indicated by its unique pharmacological profile in interacting both norepinephrine and serotonin transporter protein. The result indicated that dezocine administration significantly changed immobility time as compared to control, suggesting that dezocine may have anti-depressive effects.

Materials and Methods

Animals

C57BL/6 mice were used for this study. In some instances multiple behavioral tests were performed in a single cohort of mice: forced swim test, tail suspension test, and hot plate test were all performed on the same cohort with a week's time separated each test Animals were maintained on a 12 h light-dark cycle with food and water available ad libitum in accordance with the University of Pennsylvania Institutional Animal Care and Use Committee. Dezocine was dissolved in 0.9% saline solution and 10 µL acetic acid. The solutions were prepared immediately before use and injected intraperitoneally (i.p.). For forced swim test the drug was administered sub-chronically, 24 hours, 5 hours, and 10 minutes prior to testing.

Forced Swim Test

Mice were placed in water (30 cm depth, 23° C.) in plastic cylinders (46 cm tall×20 cm diameter) for 6 minutes. The plastic cylinders were filled with water the night before the testing in order to acclimate to room temperature. Using Viewpoint automated scoring (Viewpoint), the duration of immobility was measured. Mice were administered three injections of Dezocine before testing: one 23.5 hours before the swim test, a second injection 5 hours before the swim test, and a third injection 10 minutes before the swim test. Twenty-four mice were tested and separated into three groups. One group received three injections of saline at the three different time points. Another group received three injections 0.1 mg/kg Dezocine at the three different time points. The last group received three injections of 1.0 mg/kg Dezocine at the three different points outlined previously.

Results

Forced Swim Test Shows Anti-Depressant Activity of Dezocine

Figure 16:
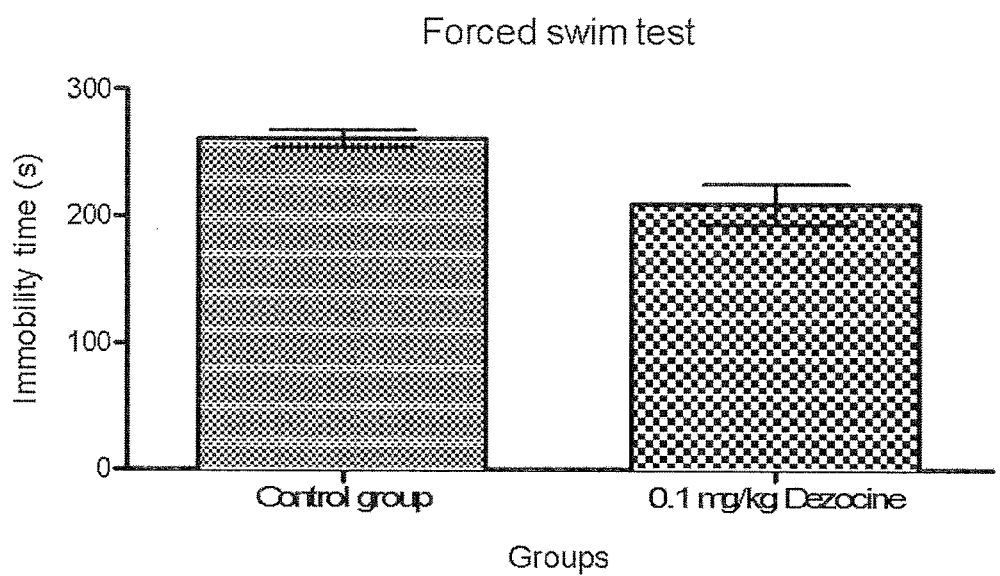
FIG. 16. Forced Swim Test: The group administered a 0.1 mg/kg dezocine dose shows lower immobility time, suggesting anti-depressant activity.
Figure 17:
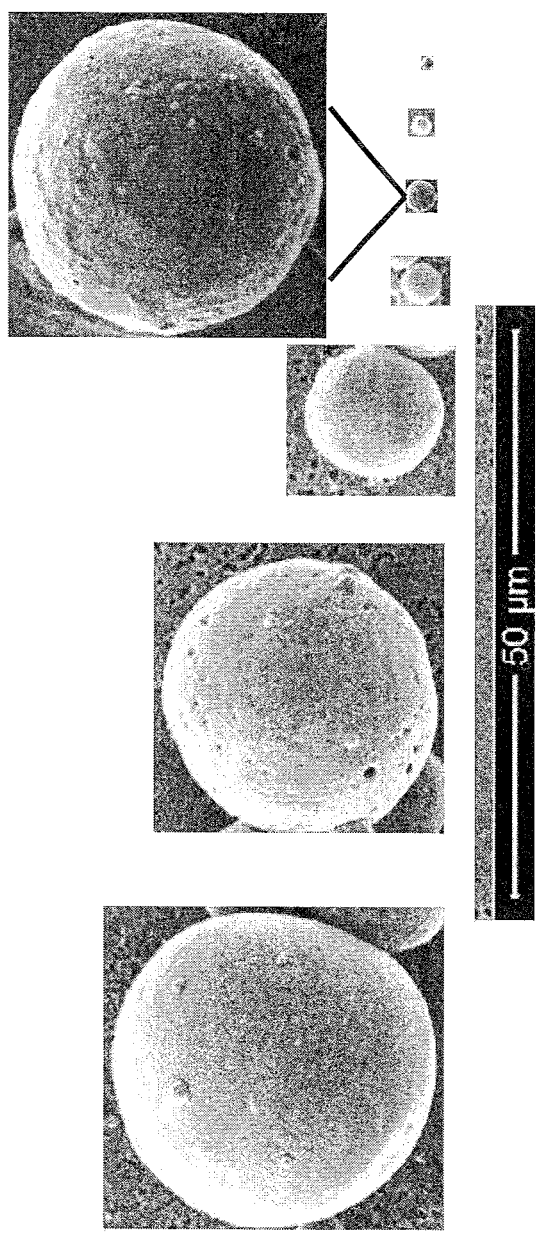
FIG. 17. Scanning electron microscope images of PVA-dezocine particles with various sizes (100 nM~25 μM) for different drug carrying and releasing properties can be generated.

After 3 injections of either dezocine (0.1 mg/kg) or saline (23.5 hr, 5 hr, and 10 min) prior to testing, the data was scored from the videos that were taken during experimentation. The data shows greatest immobility time in the 0.1 mg/kg dezocine group. There is significant difference between the saline group and the dezocine group (p<0.05) (FIG. 16).

In sum, the results show that dezocine may have anti-depressive effect and can be used to treat patients who have both pain and depression.

Example 8

Nano-Dezocine as Novel Therapeutics

This invention relates to dezocine nanoparticles, named as Nano-Dezocine, as therapeutics for pain, depression, and addiction treatment.

As discussed above, dezocine is FDA approved for pain management in the perioperative period. We recently discovered that dezocine is a serotonin and norepinephrine transporter protein inhibitor and kappa opioid receptor antagonist. It is known that dezocine is a mu opioid receptor partial agonist.

We have developed nanoparticles of dezocine, Nano-Dezocine, for clinical usages in various forms: oral, injectable, and transmucosal, including intranasal administration and other depository administration methods.

Creation of Nano-Dezocine includes two major procedures: (i) solubilizing dezocine and (ii) nano-dezocine creation.

(i) Solubilizing Dezocine

Dezocine is very hydrophobic and is not soluble in water. All solutions attempted in this experiment had concentrations ≥1 mg/mL. A formulation that was not completely soluble at ≥1 mg/mL was labeled insoluble. Dezocine was found to be insoluble in water, 5% poly(vinyl alcohol) (PVOH) solution, and 31% propylene glycol (PG) solution. Dezocine was found to be soluble at 1 mg/mL in 200-proof ethanol, but no further solutions were made with ethanol, due to its limited usefulness for medical application. Dezocine was found to be soluble at 2 mg/mL in 50% PG, but precipitated at 3 mg/mL. Dezocine was soluble at 10 mg/mL in pure PG, and no higher concentrations were attempted. When a solution of 31% PG, 1% lactic acid was used, dezocine was found to be soluble up to 30 mg/mL, which was the highest concentration attempted. All further solutions were created at about pH 4. Later parts of the experiment involving PVOH solutions found dezocine to be soluble at 10 mg/mL in a 31% PG, 6% PVOH solution buffered to pH 4. Later parts of the experiment involving PVOH solutions found dezocine to be soluble at 10 mg/mL in a 31% PG, 6% PVOH solution buffered to pH 4. No higher concentrations were attempted with this formulation.

TABLE 5

Dezocine concentrations

| Formulation | Maximum Dezocine Concentration |
|---|---|
| Water | <1 mg/mL |
| Ethanol | 1 mg/mL* |
| 5% PVA | <1 mg/mL |
| 31% Propylene Glycol | <1 mg/mL |
| 50% Propylene Glycol | 2 mg/mL |
| Propylene Glycol | 10 mg/mL |
| 31% Propylene Glycol, 1% Lactic Acid | 30 mg/mL* |

*Highest concentration attempted. Higher concentrations may be possible.

Thus, in subsequent experiments, the combination of PG and lactic acid is used to solubilize dezocine for nano-dezocine creation due to the suitability of the medical usage.

(ii) Nano-Dezocine Creation

Creating Buffer Solution

The buffer solution for this application has a pH of around 4.0, and contains propylene glycol (PG). Lactic acid was used to lower pH, and was buffered with sodium hydroxide (NaOH). In 1 mL, the buffer contains the following amounts:

| Ingredient | Amount per 1 mL |
|---|---|
| Water | 682.6 µL |
| Propylene Glycol | 310.0 µL |
| Lactic Acid | 7.4 µL |
| Sodium Hydroxide | 2.6 mg |

85% lactic acid was used for dilution, so 8.7 µL were used, and the additional volume was subtracted from the water volume, leaving 681.3 µL. A 10 M solution of NaOH was prepared for this experiment, and it was determined that 6.4 µL of the solution would provide the necessary amount of NaOH. Again, the additional volume was subtracted from the water volume. Thus, the final amounts per 1 mL were:

| Ingredient | Amount per 1 mL |
|---|---|
| Water | 674.9 µL |
| Propylene Glycol | 310.0 µL |
| Lactic Acid (85% Solution) | 8.7 µL |
| Sodium Hydroxide (10M Solution) | 6.4 µL |

These amounts are measured out using pipettes, and mixed together in test tubes using a vortex mixer. These amounts can be scaled up or down to whatever final amount of solution is desired.

Creating Poly(Vinyl Alcohol) (PVOH) Solution

First, the desired amount of water or buffer, and PVOH is measured out. A 9-10% solution is suitable for use in this application. 60 mL of buffer and 6 g of PVOH was used in this experiment. The buffer is placed in a 100-250 mL beaker along with a magnetic stir-rod, and covered in aluminum foil to prevent loss of water to evaporation. A small hole (≈0.5 cm) is poked in the aluminum foil to allow a temperature probe to be placed inside. The beaker is placed on a hot plate with the temperature probe suspended in such a way as to ensure that it is in the buffer solution, but not interfering with the stir rod or touching the glass. The solution is heated to about 85° C. with stirring. It is important to maintain within ±10° C. of this temperature during the entire process, so that the PVOH dissolves, and the water doesn't boil over. Once the temperature is high enough and stabilized, the PVOH crystals are slowly added in small amounts (≈0.5-1 g at a time). It is important to make sure the solution is constantly stirred vigorously enough to disturb the surface. This prevents the formation of a PVOH film on the surface. Once the PVOH added is completely, or almost completely dissolved, more small amounts of crystals can be added. This is repeated until all of the crystals are in the solution. The solution will become much more viscous with time. This will prevent the stir rod from being used at higher speeds, as it will seize up and begin vibrating. If this happens, the stirring is completely turned off until the rod comes to a rest, then slowly raised back up to a level lower than that at which it seized up. This entire process can take several hours. Once all of the PVOH is dissolved, the heating element and stirring mechanism can be turned off, and the beaker can be removed from the hot plate. The aluminum foil and temperature probe is removed. The stir rod can remain in the solution or be taken out. The resulting solution is a transparent, thick, viscous solution. In the several hours after being created, the solution will probably have many bubbles. If it is left to sit, these will eventually rise out of the fluid. The solution will increase in viscosity with time, so it is best to use it within a short time of creating it. This solution is covered with Parafilm or Saran wrap and stored at 4° C. for maximum shelf life.

Creating Dezocine-PVOH Solution 2 mL of buffer solution is placed in a test tube. The desired amount of dezocine is added to the buffer. In this experiment, 50 mg of dezocine were used, yielding a final solution with 10 mg/cc of dezocine. The solution is mixed with a vortex mixer until all of the dezocine is dissolved. It may be necessary to add a small amount of lactic acid to achieve high concentrations of dezocine. Once the dezocine is dissolved, 3 mL of PVOH solution is added. This is hard to do in a precise manner, because the PVOH solution is too thick for pipettes to be used. In this experiment, the PVOH solution was simply directly poured into the test tube. The pouring was done in small increments, with a wait in between each successive amount to allow all of the liquid to settle to the bottom of the tube, and allow accurate measurement of total volume. Once the solution reaches 5 mL, the tube is mixed again with the vortex until homogenized. These amounts can be scaled up or down to create various volumes of solution.

Creation of Nano-Dezocine

The dezocine-PVOH solution is placed in silicone oil at a 1:3 volume ratio of solution to oil, with around 1 µL/mL of Tween 80 added to assist disruption and homogenization. This is manually disrupted into small particles. Then, additional silicone oil is added to bring the volume ratio of solution to oil to 1:20. This is homogenized with a blender, forming a nano-emulsion. Once a water-in-oil emulsion is achieved, it is subjected to 2-3 freeze-thaw cycles of 20 hours of freezing followed by 4 hours of thawing. This will turn the dezocine-PVOH solution droplets in the emulsion into hydrogel nanoparticles of around 600-700 nm size. The solution is placed in acetone at a 1:10 volume ratio of emulsion to acetone. This is then vacuum filtered through a PTFE filter with ≈0.1 µm pore size, and then the filter is then washed with acetone to remove silicone oil residue. The nanoparticles are then collected and suspended in saline solution at whatever ratio provides the desired drug concentration.

Nano-Dezocine Formulation

Nano-Dezocine can be made in water or normal saline solution or encapsulated for various formula preparations (transmucosal, oral, implant etc.), which may include controlled release purposes. Nano-dezocine itself has mucoadhesive properties that could allow it to stay on the surface of mucosal membrane for a prolonged period of time.

Here is an example of the ingredients of Nano-Dezocine nanoparticles for intranasal administration.

| Ingredients in 10 mg/mL Dezocine Solution | | |
|---|---|---|
| Ingredient | V (µL/mL) | M (mg/mL) |
| Dezocine | 9.1 | 10.0 |
| Water | 628.4 | 628.4 |
| Propylene Glycol | 285.4 | 295.5 |

-continued

| Ingredients in 10 mg/mL Dezocine Solution | | |
|---|---|---|
| Ingredient | V (μL/mL) | M (mg/mL) |
| Polyvinyl Alcohol | 69.2 | 92.1 |
| Lactic Acid | 6.8 | 9.2 |
| Sodium Hydroxide | 1.1 | 2.4 |
| Total | 1000.0 | 1037.5 |

20% 2-Hydroxypropyl-β-cyclodextrin (HPBCD) or 20% 2-Hydroxypropyl-γ-cyclodextrin (HPGCD) as a Carrier for Dezocine In the FDA approved dezocine formulation multiple steps are needed; however, such steps are significantly reduced by dissolving dezocine in 20% 2-Hydroxypropyl-β-cyclodextrin (HPGCD) or 20% 2-Hydroxypropyl\-γ-cyclodextrin (HPBCD). Dezocine is more soluble in 20% 2-Hydroxypropyl-γ-cyclodextrin (HPGCD) (24±1 mg/mL) than in 20% 2-Hydroxypropyl-β-cyclodextrin (HPBCD) (18±1 mg/mL), where the solubility was determined as follows.

Oversaturated dezocine was dissolved in 20% 2-Hydroxypropyl-β-cyclodextrin (HPBCD) or 20% 2-Hydroxypropyl-γ-cyclodextrin (HPGCD) at room temperature, bottles were covered with aluminum foil. It was filtered with 0.2 μm PTFE syringe filter after stirring for 24 hrs.

Figure 20:
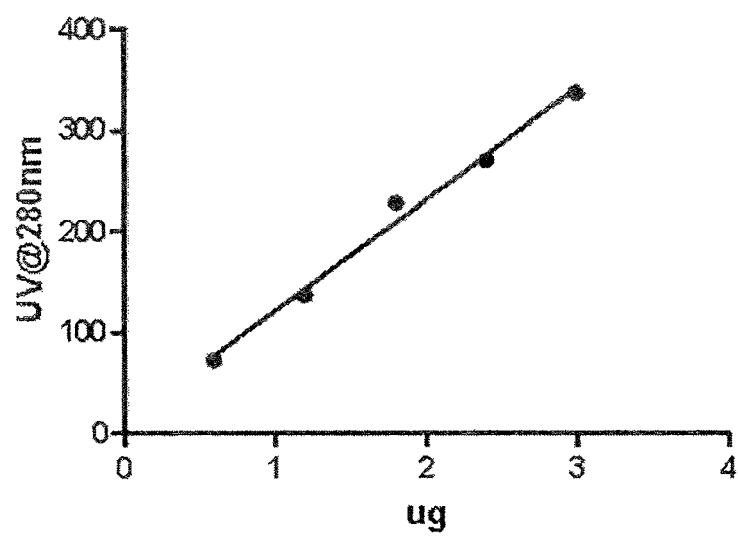
FIG. 20. Dezocine concentration calibration curve

Using 0.6 μg/μL dezocine in 100% ethanol as a standard, 1, 2, 3, 4, and 5 μL samples were injected into an HPLC with C-18 column to make a calibration curve (UV absorbance at 280 nm) (FIG. 20).

Figure 19:
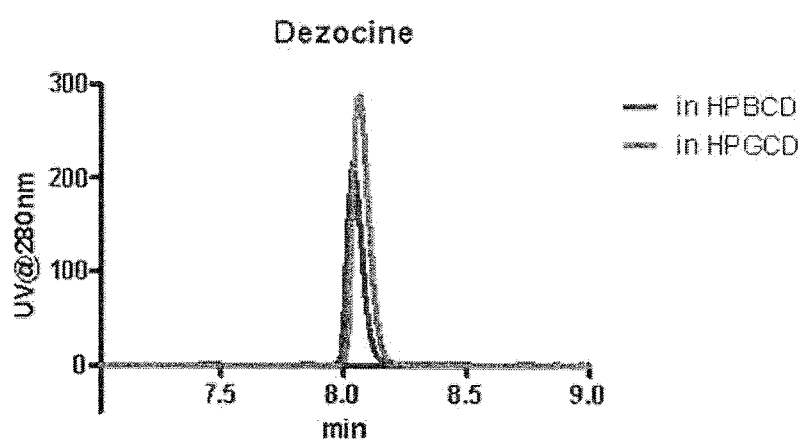
FIG. 19. HPLC chromatogram of dezocine in 20% 2-Hydroxypropyl-β-cyclodextrin (HPBCD) or 20% 2-Hydroxypropyl)-γ-cyclodextrin (HPGCD).

5 μL dezocine of each sample was injected into an HPLC and repeated 3 times (FIG. 19). The dezocine concentration was calculated from the calibration curve (FIG. 20).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating an opioid receptor associated addiction in a subject, the method comprising: administering in the form of nanoparticles to said subject a therapeutically effective amount of dezocine or a pharmaceutical composition thereof, wherein the nanoparticle size is less than or equal to 500 nm.

2. The method of claim 1, wherein the addiction is an addiction to heroin.

3. The method of claim 1, wherein said opioid receptor is a mu opioid receptor, a kappa receptor, a delta opioid receptor, or a combination thereof.

4. The method of claim 1, wherein said dezocine treats said addiction by interacting with a norepinephrine transporter (NET), a serotonin transporter (SERT), or a combination thereof.

5. The method of claim 1, wherein nanoparticle size ranges from about 5 nm to about 100 nm.

6. The method of claim 1, wherein the method further comprises administering a therapeutically effective amount of ondansetron, naltrexone, naloxone, ketamine, or a combination thereof.

7. The method of claim 1, wherein the composition is administered orally, intranasally, transmucosally, or by injection.

* * * * *

UNITED STATES PATENT AND TRADEMARK OFFICE
CERTIFICATE OF CORRECTION

PATENT NO. : 9,956,187 B2
APPLICATION NO. : 15/303221
DATED : May 1, 2018
INVENTOR(S) : Renyu Liu et al.

It is certified that error appears in the above-identified patent and that said Letters Patent is hereby corrected as shown below:

In the Specification

After Line 13, in Column 1, please insert the following:
--GOVERNMENT INTEREST STATEMENT
This invention was made with government support under grant number GM093115 awarded by the National Institutes of Health. The government has certain rights in the invention.--

Signed and Sealed this
Ninth Day of November, 2021

Drew Hirshfeld
*Performing the Functions and Duties of the
Under Secretary of Commerce for Intellectual Property and
Director of the United States Patent and Trademark Office*